(12) United States Patent
Claypool et al.

(10) Patent No.: US 8,603,101 B2
(45) Date of Patent: Dec. 10, 2013

(54) PROVISIONAL TIBIAL PROSTHESIS SYSTEM

(75) Inventors: Jody L. Claypool, Columbia City, IN (US); Steven E. Stump, Goshen, IN (US)

(73) Assignee: Zimmer, Inc., Warsaw, IN (US)

( * ) Notice: Subject to any disclaimer, the term of this patent is extended or adjusted under 35 U.S.C. 154(b) by 256 days.

(21) Appl. No.: 13/087,610

(22) Filed: Apr. 15, 2011

(65) Prior Publication Data

US 2012/0158152 A1 Jun. 21, 2012

Related U.S. Application Data

(60) Provisional application No. 61/424,222, filed on Dec. 17, 2010.

(51) Int. Cl.
*A61B 17/58* (2006.01)
*A61B 17/60* (2006.01)
*A61F 2/00* (2006.01)

(52) U.S. Cl.
USPC ........ 606/102; 606/88; 623/20.32; 623/20.15

(58) Field of Classification Search
USPC ................. 606/102; 623/20.15, 20.28, 20.25, 623/20.32
See application file for complete search history.

(56) References Cited

U.S. PATENT DOCUMENTS

| | | | |
|---|---|---|---|
| 4,501,266 A | 2/1985 | McDaniel | |
| 5,197,488 A | 3/1993 | Kovacevic | |
| 5,344,461 A | 9/1994 | Phlipot | |
| 5,360,016 A | 11/1994 | Kovacevic | |
| 5,387,239 A | 2/1995 | Bianco et al. | |
| 5,395,401 A | 3/1995 | Bahler | |
| 5,425,775 A | 6/1995 | Kovacevic et al. | |
| 5,458,637 A | 10/1995 | Hayes | |

(Continued)

FOREIGN PATENT DOCUMENTS

| | | |
|---|---|---|
| EP | 1132063 A2 | 9/2001 |
| EP | 2237177 A1 | 10/2010 |

(Continued)

OTHER PUBLICATIONS

International Search Report and Written Opinion mailed Apr. 24, 2012 in related International Application No. PCT/US2011/065683.

(Continued)

*Primary Examiner* — Andrew Yang
(74) *Attorney, Agent, or Firm* — Schwegman, Lundberg & Woessner P.A.

(57) ABSTRACT

The present disclosure provides a provisional tibial prosthesis system for a set of prosthetic knee joints for implantation in a natural knee, the provisional tibial prosthesis system including a bearing component and a bearing support, the spacing of the bearing component from the bearing support is adjustable to allow for representation of a variety of different sized final tibial prostheses. In this system, only one provisional bearing component corresponding to each level of constraint is needed and shims are used to adjust the spacing of the bearing component from the bearing support. The shims are slidably insertable between the bearing component and the bearing support in an anterior/posterior direction to allow for adjustment of the spacing of the bearing component from the bearing support. The number of provisional components needed during knee surgery is reduced and adjustment of the system only requires the knee joint to be distracted by a distance equal to the height of a particular shim.

21 Claims, 18 Drawing Sheets

(56) References Cited

U.S. PATENT DOCUMENTS

| | | | |
|---|---|---|---|
| 5,470,354 A | 11/1995 | Hershberger et al. | |
| 5,489,311 A | 2/1996 | Cipolletti | |
| 5,571,194 A | 11/1996 | Gabriel | |
| 5,609,645 A | 3/1997 | Vinciuerra | |
| 5,656,785 A | 8/1997 | Trainor et al. | |
| 5,658,341 A | 8/1997 | Delfosse | |
| 5,702,464 A | 12/1997 | Lackey et al. | |
| 5,733,292 A * | 3/1998 | Gustilo et al. | 606/88 |
| 5,776,200 A | 7/1998 | Johnson et al. | |
| 5,782,925 A | 7/1998 | Collazo et al. | |
| 5,871,541 A | 2/1999 | Gerber | |
| 5,976,147 A | 11/1999 | LaSalle et al. | |
| 6,607,559 B2 | 8/2003 | Ralph et al. | |
| 6,632,225 B2 | 10/2003 | Sanford et al. | |
| 6,702,821 B2 | 3/2004 | Bonutti | |
| 6,743,258 B1 | 6/2004 | Keller | |
| 6,770,078 B2 | 8/2004 | Bonutti | |
| 6,942,670 B2 | 9/2005 | Heldreth et al. | |
| 6,974,481 B1 | 12/2005 | Carson | |
| 7,309,363 B2 | 12/2007 | Dietz | |
| 7,412,897 B2 | 8/2008 | Crottet et al. | |
| 7,442,196 B2 | 10/2008 | Fisher et al. | |
| 7,488,330 B2 | 2/2009 | Stad | |
| 7,547,327 B2 | 6/2009 | Collazo | |
| 7,575,602 B2 | 8/2009 | Amirouche et al. | |
| 7,578,821 B2 | 8/2009 | Fisher et al. | |
| 7,587,945 B2 | 9/2009 | Crottet et al. | |
| 7,591,854 B2 | 9/2009 | Wasielewski | |
| 7,632,283 B2 | 12/2009 | Heldreth | |
| 7,632,314 B2 | 12/2009 | Dietz | |
| 7,695,520 B2 | 4/2010 | Metzger et al. | |
| 7,837,691 B2 | 11/2010 | Cordes et al. | |
| 7,850,698 B2 | 12/2010 | Straszheim-Morley et al. | |
| 8,065,927 B2 | 11/2011 | Crottet et al. | |
| 8,141,437 B2 | 3/2012 | Amirouche et al. | |
| 8,197,549 B2 | 6/2012 | Amirouche et al. | |
| 8,211,041 B2 | 7/2012 | Fisher et al. | |
| 8,491,589 B2 | 7/2013 | Fisher et al. | |
| 8,506,571 B2 | 8/2013 | Chana et al. | |
| 2002/0058997 A1 | 5/2002 | O'Connor et al. | |
| 2004/0064191 A1 | 4/2004 | Wasielewski | |
| 2004/0167537 A1 | 8/2004 | Errico et al. | |
| 2004/0225368 A1 | 11/2004 | Plumet et al. | |
| 2005/0055102 A1 | 3/2005 | Tornier et al. | |
| 2005/0267485 A1 | 12/2005 | Cordes et al. | |
| 2006/0020343 A1 | 1/2006 | Ek | |
| 2006/0069436 A1 | 3/2006 | Sutton et al. | |
| 2006/0184176 A1 | 8/2006 | Straszheim-Morley et al. | |
| 2006/0190087 A1 | 8/2006 | O'Connor | |
| 2006/0239922 A1 | 10/2006 | Cooper | |
| 2007/0123992 A1 | 5/2007 | Sanford | |
| 2007/0239165 A1 | 10/2007 | Amirouche | |
| 2008/0051908 A1 | 2/2008 | Angibaud et al. | |
| 2008/0103603 A1 | 5/2008 | Hintermann | |
| 2009/0125114 A1 | 5/2009 | May et al. | |
| 2009/0204222 A1 | 8/2009 | Burstein et al. | |
| 2009/0259314 A1 | 10/2009 | Linder-Ganz et al. | |
| 2009/0264894 A1 | 10/2009 | Wasielewski | |
| 2009/0287310 A1 | 11/2009 | Fisher et al. | |
| 2009/0306787 A1 | 12/2009 | Crabtree et al. | |
| 2010/0010494 A1 | 1/2010 | Quirno | |
| 2010/0063595 A1 | 3/2010 | Dietz | |
| 2010/0076563 A1 | 3/2010 | Otto et al. | |
| 2010/0082111 A1 | 4/2010 | Thomas | |
| 2010/0100011 A1 | 4/2010 | Roche | |
| 2010/0198275 A1 | 8/2010 | Chana et al. | |
| 2010/0249102 A1 | 9/2010 | Rock et al. | |
| 2011/0100011 A1 | 5/2011 | Staffend | |
| 2012/0095563 A1 | 4/2012 | Sanford et al. | |
| 2012/0179069 A1 | 7/2012 | Amirouche | |
| 2012/0232429 A1 | 9/2012 | Fischer et al. | |
| 2012/0290088 A1 | 11/2012 | Amirouche et al. | |
| 2013/0013076 A1 | 1/2013 | Fisher et al. | |
| 2013/0096567 A1 | 4/2013 | Fisher et al. | |
| 2013/0102929 A1 | 4/2013 | Haight et al. | |
| 2013/0103038 A1 | 4/2013 | Fischer et al. | |

FOREIGN PATENT DOCUMENTS

| | | |
|---|---|---|
| WO | WO-2010022272 A1 | 2/2010 |
| WO | WO2010/023062 A2 | 3/2010 |
| WO | WO-2012004580 A1 | 1/2012 |
| WO | WO-2012020460 A1 | 2/2012 |

OTHER PUBLICATIONS

Zimmer Patient Specific Instruments, Surgical Techniques for NexGen Complete Knee Solution, Zimmer, Inc., 2010.

Zimmer NexGen Trabecular Metal Tibial Tray, Surgical Technique, Zimmer, Inc. 2007, 2009.

"International Application Serial No. PCT/US2011/064435, Search Report mailed Jun. 21, 2012", 5 pgs.

"International Application Serial No. PCT/US2011/065683, International Search Report mailed Apr. 24, 2012", 12 pgs.

"International Application Serial No. PCT/US2011/065683, Written Opinion mailed Apr. 24, 2012", 10 pgs.

"International Application Serial No. PCT/US2011/064435, International Preliminary Report on Patentability mailed Jun. 27, 2013", 9 pgs.

"International Application Serial No. PCT/US2011/064435, Written Opinion mailed Jun. 21, 2012", 7 pgs.

"International Application Serial No. PCT/US2011/065683, International Preliminary Report on Patentability mailed Jun. 27, 2013", 11 pgs.

"International Application Serial No. PCT/US2013/034286, International Search Report mailed Jun. 25, 2013", 6 pgs.

"International Application Serial No. PCT/US2013/034286, Written Opinion mailed Jun. 25, 2013", 6 pgs.

"International Application Serial No. PCT/US2013/034293, International Search Report mailed Jun. 25, 2013", 6 pgs.

"International Application Serial No. PCT/US2013/034293, Written Opinion mailed Jun. 25, 2013", 7 pgs.

* cited by examiner

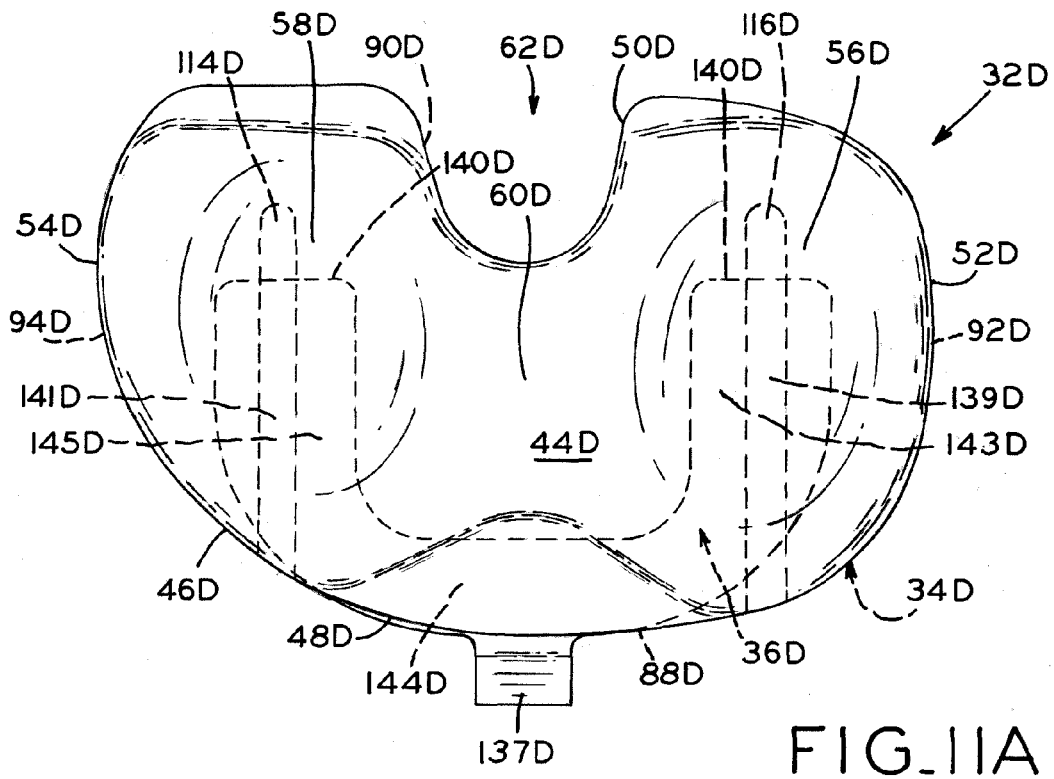
FIG_11A
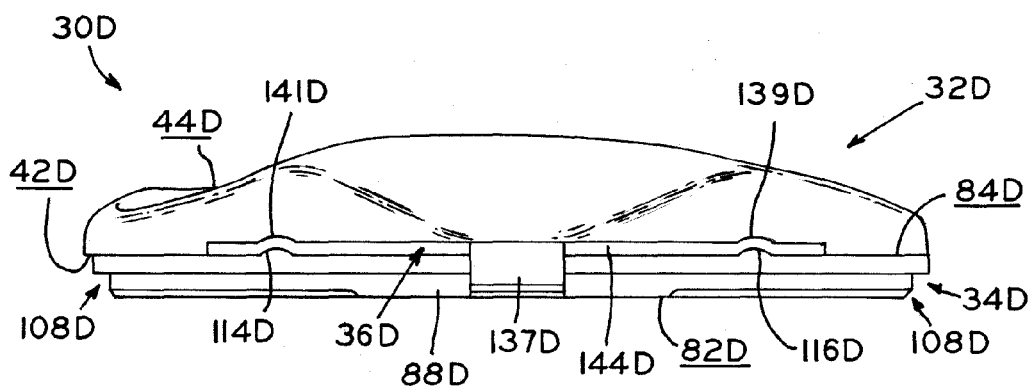
FIG_11B

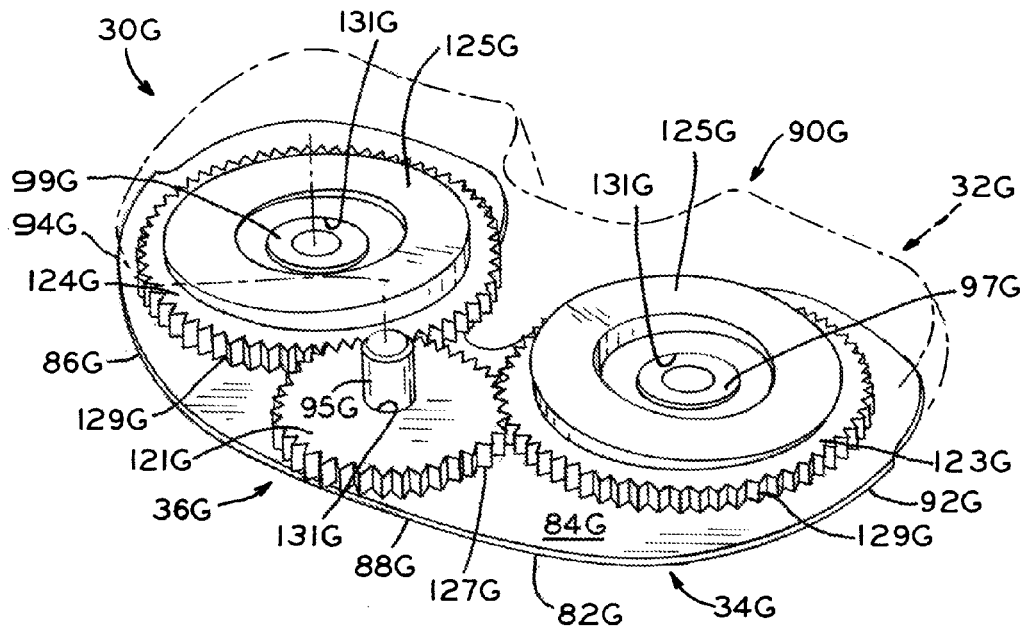
FIG_14
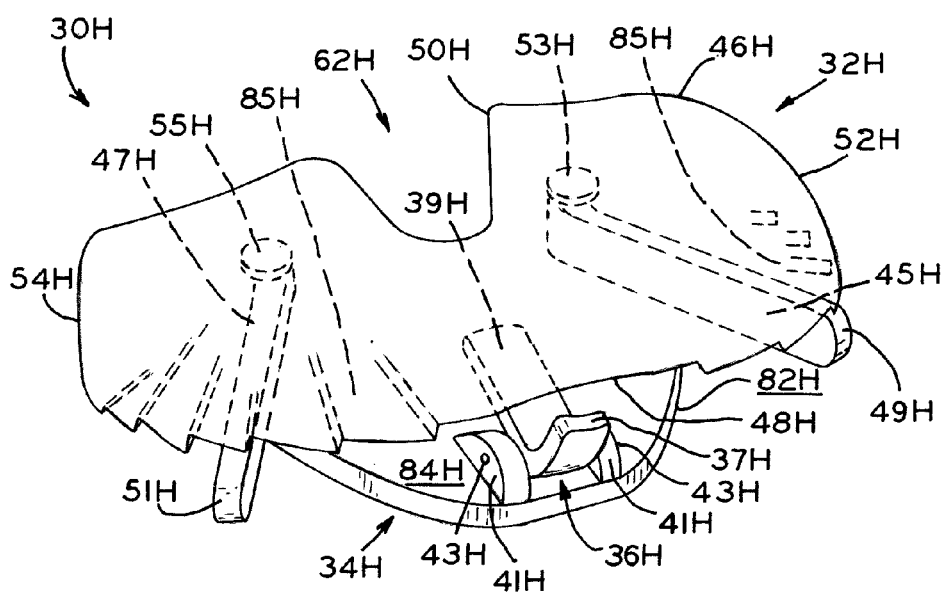
FIG_15

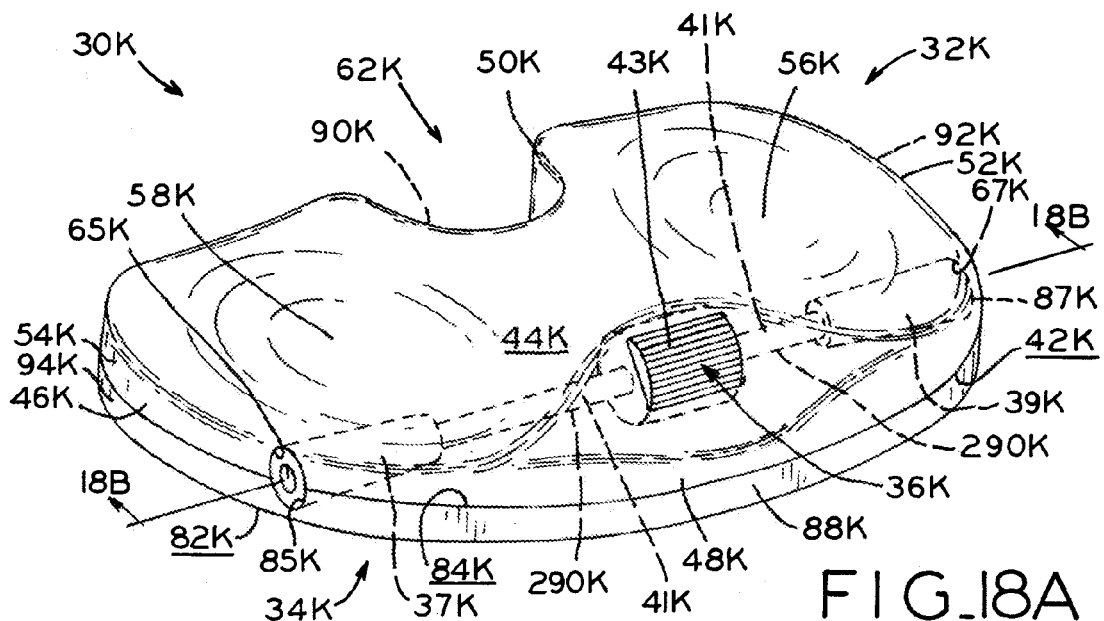
FIG_18A
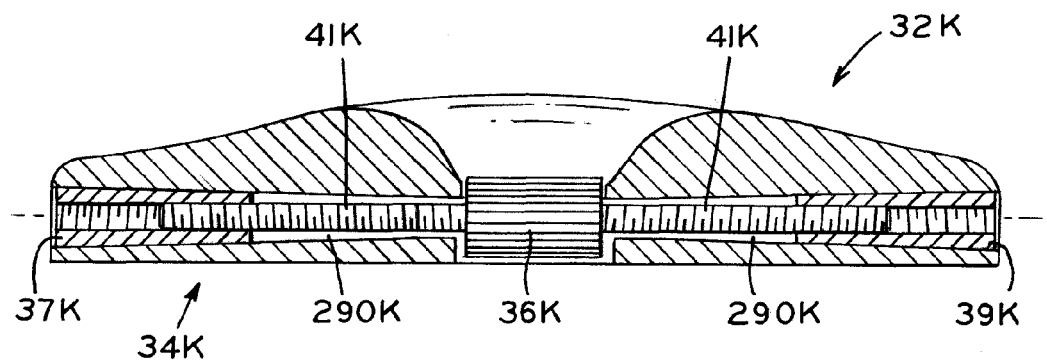
FIG_18B

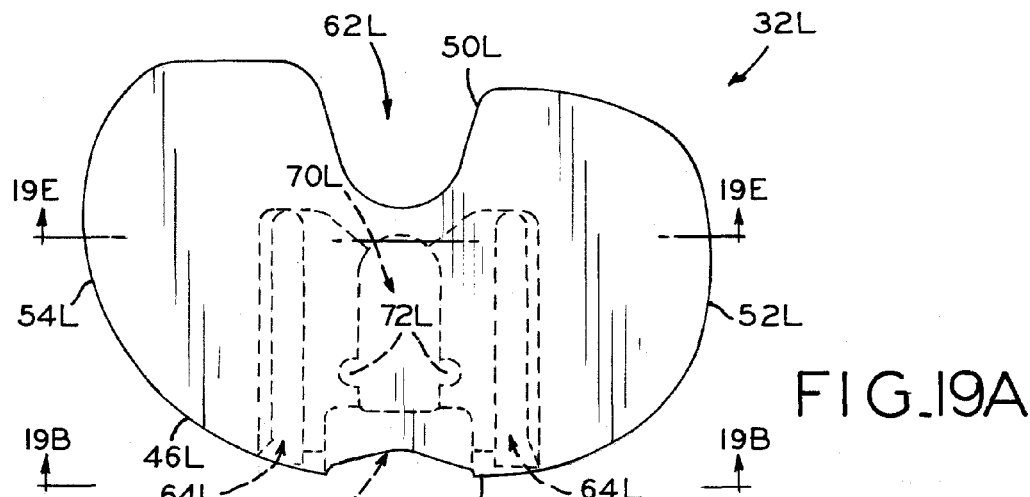
FIG_19A
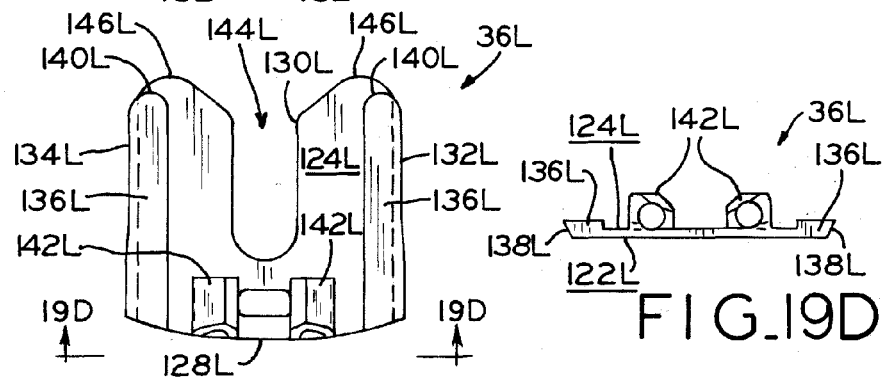
FIG_19C  FIG_19D
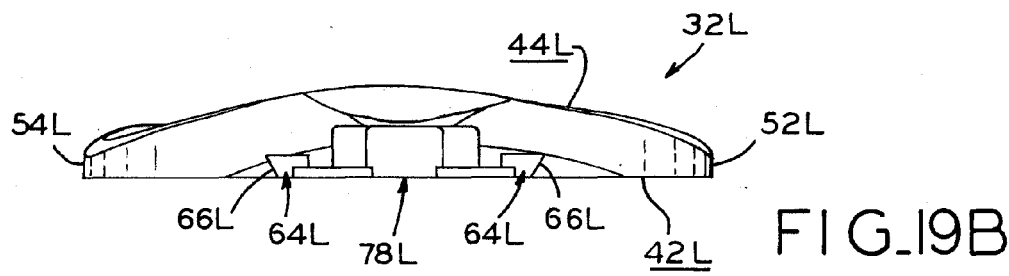
FIG_19B
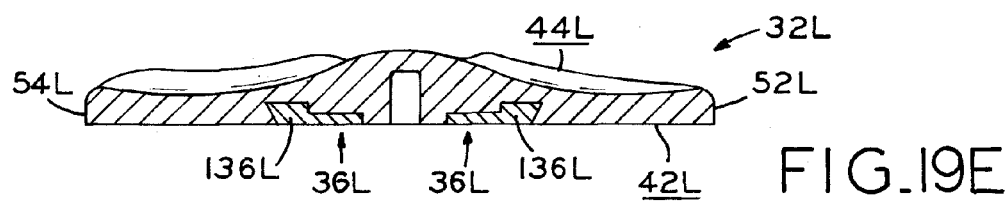
FIG_19E

PROVISIONAL TIBIAL PROSTHESIS SYSTEM

CROSS-REFERENCE TO RELATED APPLICATIONS

This application claims priority to U.S. Provisional Patent Application Ser. No. 61/424,222, filed Dec. 17, 2010, the entire disclosure of which is hereby expressly incorporated by reference herein.

BACKGROUND

1. Field of the Disclosure

The present disclosure relates generally to provisional orthopedic components used to replicate final orthopedic components during a surgical procedure. More particularly, the present disclosure relates to provisional tibial components that assist in determining the proper size of a final tibial prosthesis for a prosthetic knee joint for replacement of all or part of a natural knee.

2. Description of the Related Art

Knee replacement provisional components are positioned on a distal femur and/or a proximal tibia to allow range of motion testing so that a surgeon can verify proper sizing of final prosthetic components. Knee replacement systems may include a wide variety of tibial bearing components, including bearing components which cooperate to form a posterior stabilized prosthesis, a cruciate retaining knee prosthesis or a knee prosthesis having an intermediate level of constraint between a posterior stabilized and cruciate retaining prosthesis. Such systems include a high number of provisional components corresponding to the differing constraint levels offered by the system as well as the different sized bearings for each constraint level. During knee surgery, a surgeon may remove and replace a provisional tibial bearing component of a first size with a provisional tibial bearing component of a second size to adjust the ligament tension of the knee joint. Efforts have been made to lessen the number of provisional components needed during knee surgery, including the use of adjustable tibial components having an adjustable height to allow the adjustable tibial component to mimic a variety of different sized final tibial prostheses.

One such device includes a spacer block positioned between a provisional bearing component and a tibial tray to provide additional spacing of the provisional bearing from the tibial tray. However, these devices require distraction of the knee joint to secure the spacer block to the bearing component and the tibia tray.

SUMMARY

The present disclosure provides a provisional tibial prosthesis system for a set of prosthetic knee joints for implantation in a natural knee, the provisional tibial prosthesis system including a bearing component and a bearing support, the spacing of the bearing component from the bearing support is adjustable to allow for representation of a variety of different sized final tibial prostheses. In a provisional tibial prosthesis system there is, among other things, a bearing surface that articulates with a femoral prosthesis component. Knee replacement systems may include a wide variety of bearing components, including bearing components which cooperate to form a posterior stabilized prosthesis, a cruciate retaining knee prosthesis or a knee prosthesis having an intermediate level of constraint between a posterior stabilized and cruciate retaining prosthesis. In the system of the present disclosure, instead of a system that includes a high number of provisional components corresponding to the differing constraint levels offered by the system as well as the different sized bearings for each constraint level, only one provisional bearing component corresponding to each level of constraint is needed and shims are used to adjust the spacing of the bearing component from the bearing support. Advantageously, the number of provisional components needed during knee surgery is reduced and adjustment of the system only requires the knee joint to be distracted by a distance equal to the height of a particular shim.

In one embodiment, the present disclosure includes a plurality of shims slidably insertable between a bearing component and a bearing support in an anterior/posterior direction to allow for adjustment of the spacing of the bearing component from the bearing support. Advantageously, the present disclosure provides a provisional tibial prosthesis system which can be adjusted without removing the bearing component and the bearing support from the knee joint and only distracting the knee joint a distance equal to the height of a particular shim. In one embodiment, the shims are available in a variety of heights to vary the spacing of the bearing component from the bearing support. In other embodiments, the shims are available in equal heights for shim stacking.

In one embodiment of the present disclosure, a surgeon can space a bearing component having a bearing component height from a bearing support by sliding a first shim having a first shim height between the bearing component and the bearing support in the anterior/posterior direction, and subsequently perform range of motion testing of the knee joint to verify proper sizing of the provisional tibial prosthesis system. If the provisional tibial prosthesis system is properly sized with the first shim between the bearing component and the bearing support, a first final tibial prosthesis represented by the first shim height and the bearing height can be selected for implantation in the natural knee. If the provisional tibial prosthesis system is not properly sized, the surgeon can remove the first shim from between the bearing component and the bearing support in the anterior/posterior direction, and space the bearing component from the bearing support by sliding a second shim having a second shim height between the bearing component and the bearing support in the anterior/posterior direction. If the provisional tibial prosthesis system is properly sized with the second shim between the bearing component and the bearing support, a second final tibial prosthesis represented by the second shim height and the bearing height can be selected for implantation in the natural knee. In another embodiment, if the provisional tibial prosthesis system is not properly sized with the first shim between the bearing component and the bearing support, a second shim having a second shim height can be used to space the bearing component from the bearing support by sliding the second shim between the bearing component and the bearing support in the anterior/posterior direction with the first shim also between the bearing component and the bearing support. If the provisional tibial prosthesis system is properly sized with the first shim and the second shim between the bearing component and the bearing support, a third final tibial prosthesis represented by the first shim height, the second shim height, and the bearing height can be selected for implantation in the natural knee. This stacking of the shims can be repeated using a variety of shims having equal or varying height.

The disclosure, in one form thereof, comprises a provisional tibial prosthesis system for a prosthetic knee joint for implantation in a natural knee, the provisional tibial prosthesis system capable of alternatively mimicking the geometry of a first final tibial prosthesis and a second final tibial prosthesis, the natural knee comprising a proximal tibia and a distal femur and having a medial/lateral axis, an anterior/posterior axis, and a proximal/distal axis, the medial/lateral axis corresponding to a medial/lateral direction, the anterior/posterior axis corresponding to an anterior/posterior direction, and the proximal/distal axis corresponding to a proximal/distal direction, the provisional tibial prosthesis system including a tibial base plate having a bone contacting surface and an opposing base plate superior surface; a tibial bearing component having a tibial bearing component height, the tibial bearing component attachable to the tibial base plate, the tibial bearing component height representing the first final tibial prosthesis; and a shim having a shim height, the shim slidable relative to both the tibial base plate and the tibial bearing component to be slidably receivable between the tibial base plate and the tibial bearing component in the anterior/posterior direction when the tibial base plate and the tibial bearing component are separated by a distance along the proximal/distal axis equal to the shim height, the shim height cooperating with the tibial bearing component height to represent the second final tibial prosthesis.

The disclosure, in another form thereof, comprises a provisional tibial prosthesis system for a prosthetic knee joint for implantation in a natural knee, the provisional tibial prosthesis system capable of alternatively mimicking the geometry of a first final tibial prosthesis, a second final tibial prosthesis, and a third final tibial prosthesis, the natural knee comprising a proximal tibia and a distal femur and having a medial/lateral axis, an anterior/posterior axis, and a proximal/distal axis, the medial/lateral axis corresponding to a medial/lateral direction, the anterior/posterior axis corresponding to an anterior/posterior direction, and the proximal/distal axis corresponding to a proximal/distal direction, the provisional tibial prosthesis system including a tibial base plate having a bone contacting surface and an opposing base plate superior surface; a tibial bearing component having a tibial bearing component height, the tibial bearing component attachable to the tibial base plate, the tibial bearing component height representing the first final tibial prosthesis; a first shim having a first shim height, the first shim slidable relative to both the tibial base plate and the tibial bearing component to be slidably receivable between the tibial base plate and the tibial bearing component in the anterior/posterior direction when the tibial base plate and the tibial bearing component are separated by a first distance along the proximal/distal axis equal to the first shim height, the first shim height cooperating with the tibial bearing component height to represent the second final tibial prosthesis; and a second shim having a second shim height, the second shim slidable relative to both the tibial base plate and the tibial bearing component to be slidably receivable between the tibial base plate and the tibial bearing component in the anterior/posterior direction when the tibial base plate and the tibial bearing component are separated by a second distance along the proximal/distal axis equal to the first shim height and the second shim height, the first shim height and the second shim height cooperating with the tibial bearing component height to represent the third final tibial prosthesis.

The disclosure, in a further form thereof, comprises a method of determining a size of a final tibial prosthesis for a prosthetic knee joint for implantation in a natural knee, the natural knee comprising a proximal tibia and a distal femur and having a medial/lateral axis, an anterior/posterior axis, and a proximal/distal axis, the medial/lateral axis corresponding to a medial/lateral direction, the anterior/posterior axis corresponding to an anterior/posterior direction, and the proximal/distal axis corresponding to a proximal/distal direction, the method including: selecting a provisional tibial prosthesis system including a tibial base plate having a bone contacting surface and an opposing base plate superior surface; a tibial bearing component having a tibial bearing component height, the tibial bearing component attachable to the tibial base plate; and a first shim having a first shim height, the first shim slidable relative to both the tibial base plate and the tibial bearing component to be slidably receivable between the tibial base plate and the tibial bearing component in the anterior/posterior direction when the tibial base plate and the tibial bearing component are separated by a first distance along the proximal/distal axis equal to the first shim height; resecting the proximal tibia to form a resected proximal tibia surface; positioning the bone contacting surface of the tibial base plate on the resected proximal tibia surface; positioning the tibial bearing component on the tibial base plate; and spacing the tibial bearing component from the tibial base plate by sliding the first shim between the tibial base plate and the tibial bearing component in the anterior/posterior direction, without distracting the femur from the tibia a distance greater than the first shim height.

BRIEF DESCRIPTION OF THE DRAWINGS

The above-mentioned and other features and advantages of this disclosure, and the manner of attaining them, will become more apparent and the disclosure itself will be better understood by reference to the following descriptions of embodiments of the disclosure taken in conjunction with the accompanying drawings, wherein:

FIG. 11A is a plan view of a provisional tibial prosthesis system in accordance with an exemplary fourth embodiment of the present disclosure;

FIG. 11B is a front elevation view of the provisional tibial prosthesis system of FIG. 11A;

FIG. 14 is a partial perspective view of a provisional tibial prosthesis system in accordance with an exemplary seventh embodiment of the present disclosure;

FIG. 15 is a perspective view of a provisional tibial prosthesis system in accordance with an exemplary eighth embodiment of the present disclosure;

FIG. 18A is a perspective view of a provisional tibial prosthesis system in accordance with an exemplary eleventh embodiment of the present disclosure;

FIG. 18B is a partial cross-sectional view taken along line 18B-18B of FIG. 18A;

FIG. 19A is a plan view of a tibial bearing component in accordance with another exemplary embodiment of the present disclosure;

FIG. 19B is a front elevation view of the tibial bearing component of FIG. 19A;

FIG. 19C is a plan view of a shim in accordance with another exemplary embodiment of the present disclosure;

FIG. 19D is a front elevation view of the shim of FIG. 19C; and

FIG. 19E is a cross-sectional view taken along line 19E-19E of FIG. 19A illustrating the shim of FIG. 19C positioned within a recess of the tibial bearing component of FIG. 19A.

Corresponding reference characters indicate corresponding parts throughout the several views. The exemplifications set out herein illustrate exemplary embodiments of the disclosure, and such exemplifications are not to be construed as limiting the scope of the disclosure in any manner.

DETAILED DESCRIPTION

The present disclosure provides a provisional tibial prosthesis system for a set of prosthetic knee joints for implantation in a natural knee, the provisional tibial prosthesis system including a bearing component and a bearing support, the spacing of the bearing component from the bearing support is adjustable to allow for representation of a variety of different sized final tibial prostheses.

The provisional tibial prosthesis system of the present disclosure may be used with a final tibial prosthesis in accordance with the tibial prosthesis described in U.S. Patent Application Ser. No. 61/381,800, filed Sep. 10, 2010, entitled "Tibial Prosthesis Facilitating Rotational Alignment," the entire disclosure of which is hereby expressly incorporated herein by reference. Further, the provisional tibial prosthesis system of the present disclosure may be used with the method and apparatus described in U.S. Patent Application Ser. No. 61/424,222, filed Dec. 17, 2010, entitled "User Interface Related to a Surgical Provisional," the entire disclosure of which was previously incorporated herein by reference.

Figure 6:
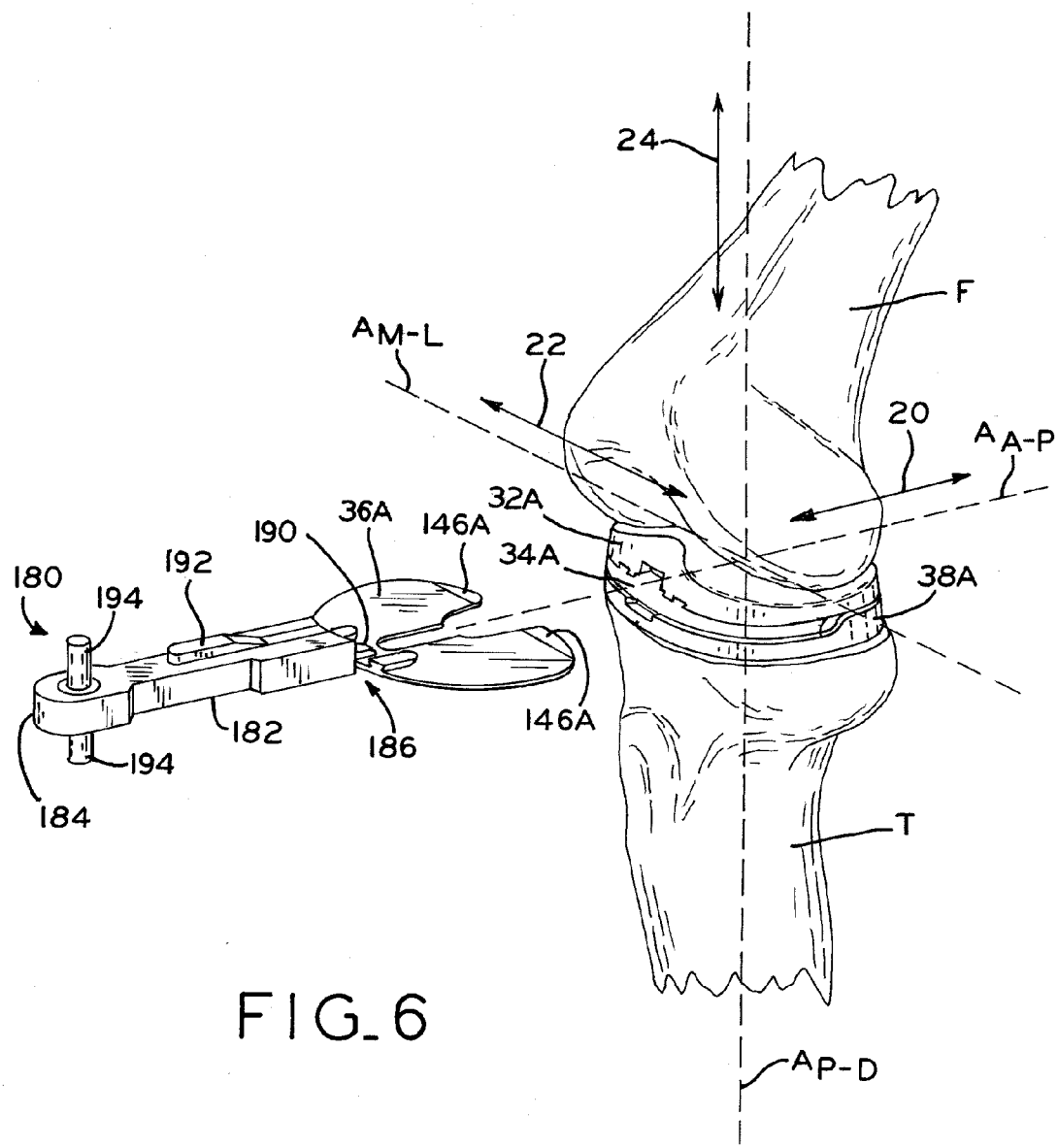
FIG. 6 is a perspective view of a knee joint and the provisional tibial prosthesis system of FIG. 1 illustrating a resected proximal tibia surface with the tibial base plate of FIG. 5 attached thereon, the base component of FIG. 3A positioned on the tibial base plate, the tibial bearing component of FIG. 2A attached to the base component, and a surgical instrument connected to the shim of FIG. 4A, and illustrating axes of the knee joint.

FIG. 6 illustrates a natural knee comprising proximal tibial T and distal femur F. FIG. 6 depicts a coordinate system of the natural knee including anterior/posterior axis $A_{A-P}$, medial/lateral axis $A_{M-L}$, and proximal/distal axis $A_{P-D}$. Anterior/posterior axis $A_{A-P}$ corresponds to anterior/posterior direction 20, medial/lateral axis $A_{M-L}$ corresponds to medial/lateral direction 22, and proximal/distal axis $A_{P-D}$ corresponds to proximal/distal direction 24. Anterior/posterior direction 20, medial/lateral direction 22, and proximal/distal direction 24 are each normal to one another. As used herein, "proximal" refers to a direction generally toward the heart of a patient, and "distal" refers to the opposite direction of proximal, i.e., away from the heart of the patient. Further, as used herein, "anterior" refers to a direction generally toward the front of a patient, and "posterior" refers to the opposite direction of anterior, i.e., toward the back of a patient. As used herein, "medial" refers to a direction generally toward the middle of a patient, and "lateral" refers to the opposite direction of medial, i.e., toward the side of a patient. For purposes of this disclosure, the above-mentioned anatomical references are used in the description of the components of the provisional tibial prosthesis system with reference to a desired operable use of the components in the body.

While the exemplary embodiments detailed herein are shown and described with regard to a left knee, it will be appreciated that the present disclosure is equally applicable to a right knee configuration.

Figure 1:
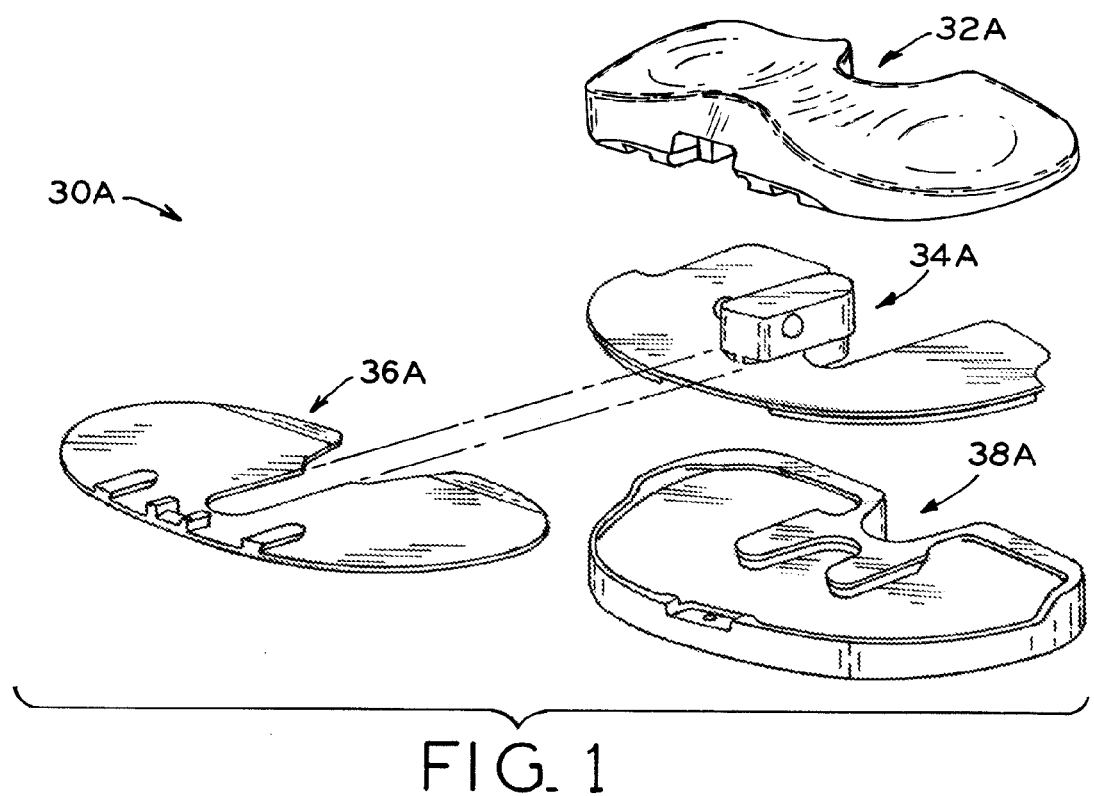
FIG. 1 is an exploded perspective view of a provisional tibial prosthesis system in accordance with an exemplary first embodiment of the present disclosure.

The disclosed embodiments of the present disclosure include a tibial bearing component and a base component. For example, as shown in FIG. 1 of an exemplary first embodiment, provisional tibial prosthesis system 30A includes tibial bearing component 32A and base component 34A. Reference numbers for the provisional tibial prosthesis system, the tibial bearing component, and the base component utilize the same numerical reference number combined with different letters to distinguish the exemplary embodiment (i.e., tibial bearing component 32A, 32B, 32C, etc. respectively correspond to the first, second, and third exemplary embodiments, etc.). For the purposes of this disclosure, a reference numeral followed by A-K corresponds to a similar feature between the exemplary first through eleventh embodiments, respectively.

Figure 2A:
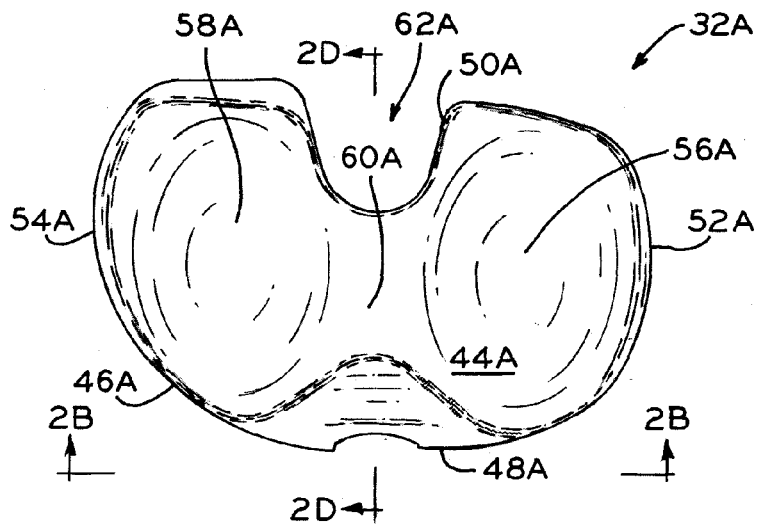
FIG. 2A is a plan view of a tibial bearing component of the provisional tibial prosthesis system of FIG. 1.

The common elements between the eleven described exemplary embodiments follow a similar reference number labeling scheme. For example, the first exemplary embodiment, as illustrated in FIGS. 2A-2D, includes tibial bearing component 32A generally including tibial bearing component inferior surface 42A, opposing tibial bearing component superior surface 44A, and tibial bearing component peripheral wall 46A extending from inferior surface 42A to superior surface 44A. Tibial bearing component 32A includes bearing anterior side 48A, bearing posterior side 50A, bearing lateral side 52A, and bearing medial side 54A. Superior surface 44A is adapted to articulate with condyles of a distal femur F (shown in FIGS. 6-8), or condyles of a femoral component (not shown) secured to a distal end of a femur. Superior surface 44A includes bearing lateral articular surface 56A in bearing lateral side 52A and bearing medial articular surface 58A in bearing medial side 54A, with central tibial eminence 60A disposed between bearing articular surfaces 56A, 58A. Referring to FIG. 2A, eminence 60A generally corresponds in shape and size with the natural tibial eminence of a proximal tibial T (shown in FIGS. 6-8) prior to resection. Tibial bearing component 32A further includes PCL cut-out 62A disposed at posterior side 50A between lateral articular surface 56A and medial articular surface 58A. PCL cut-out 62A is sized and positioned to correspond with a posterior cruciate retaining ligament of a knee joint.

In the exemplary embodiment of FIGS. 2A-2D, tibial bearing component 32A is illustrated as a cruciate retaining bearing component though it is contemplated that other tibial bearing components may be utilized in accordance with the present disclosure such as bearing components which cooperate to form a posterior stabilized prosthesis or a knee prosthesis having an intermediate level of constraint between a posterior stabilized and cruciate retaining prosthesis. Tibial bearing component 32A may also be made available in a variety of shapes and sizes to accommodate a variety of knee joints.

Figure 2B:
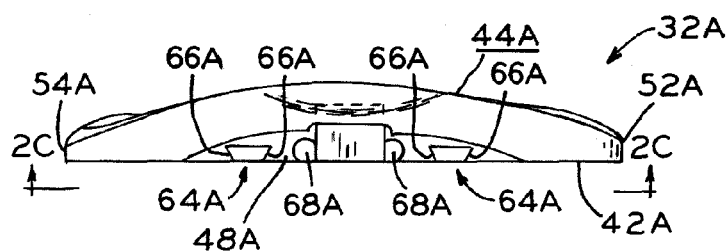
FIG. 2B is a front elevation view of the tibial bearing component of FIG. 2A.
Figure 2C:
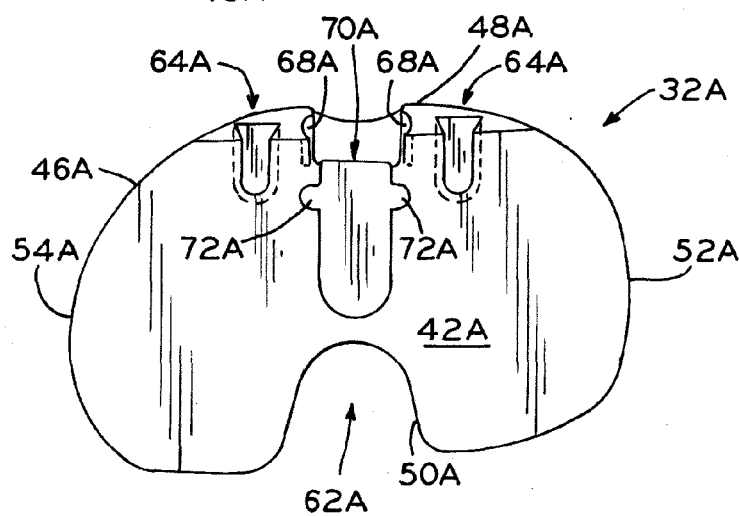
FIG. 2C is a bottom view of the tibial bearing component of FIG. 2A.
Figure 2D:
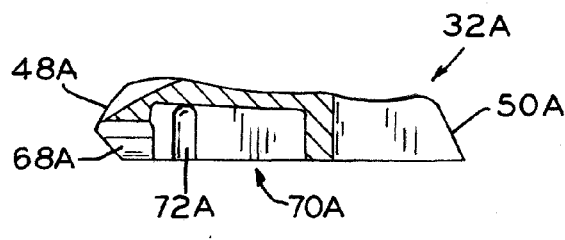
FIG. 2D is a cross-sectional view taken along line 2D-2D of FIG. 2A.

As shown in FIGS. 2A-2D, tibial bearing inferior surface 42A of tibial bearing component 32A includes slots 64A, alignment pins 68A, bearing cavity 70A, and bearing nub cavities 72A. As illustrated in FIGS. 2B and 2C, slots 64A are exposed at anterior side 48A and extend from anterior side 48A toward posterior side 50A within tibial bearing component 32A in a direction parallel to anterior/posterior axis $A_{A-P}$. As shown in FIG. 2B, in an exemplary embodiment, slots 64A have tapering walls 66A. Referring to FIGS. 2B and 2C, alignment pins 68A are located between slots 64A at anterior side 48A. Bearing cavity 70A extends from inferior surface 42A towards superior surface 44A and is sized to accept protrusion 96A (shown in FIG. 3A) of base component 34A. Further, bearing cavity 70A includes bearing nub cavities 72A which extend on opposing sides of bearing cavity 70A and are each sized to receive a nub 104A (shown in FIG. 3A) located on protrusion 96A of base component 34A.

Figure 3A:
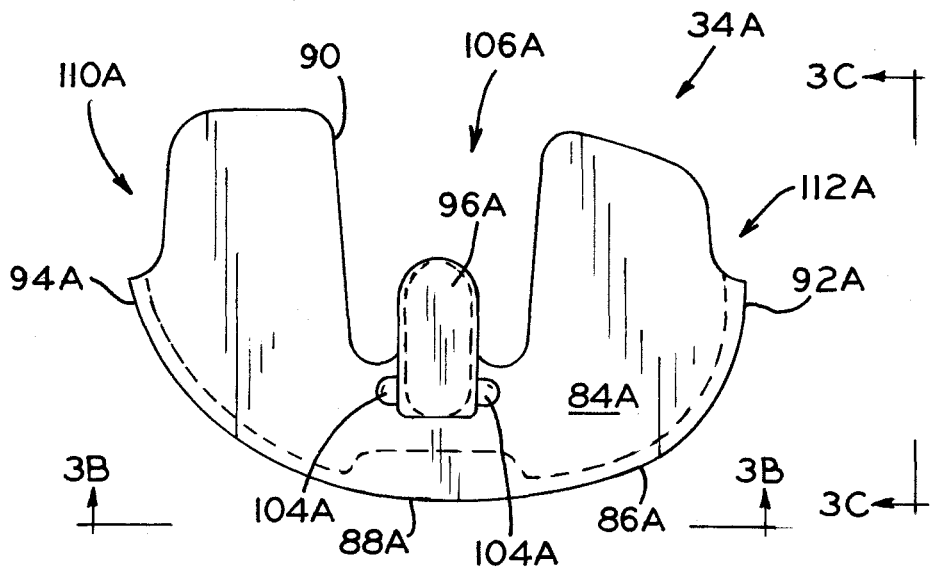
FIG. 3A is a plan view of a base component of the provisional tibial prosthesis system of FIG. 1.
Figure 3B:
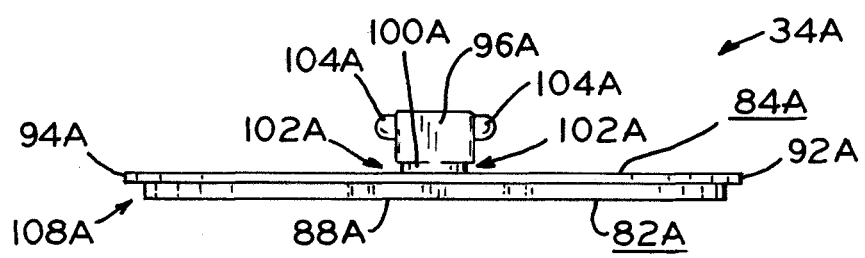
FIG. 3B is a front elevation view of the base component of FIG. 3A.
Figure 3C:
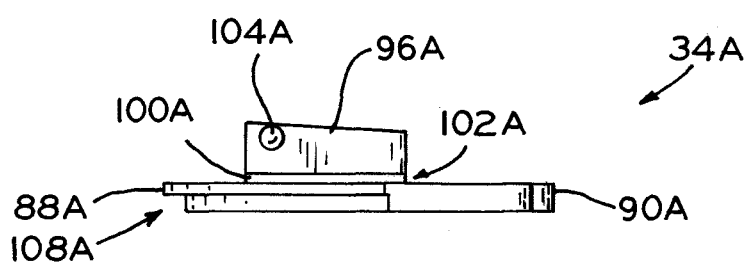
FIG. 3C is a side elevation view of the base component of FIG. 3A.

The first exemplary embodiment, as illustrated in FIGS. 3A-3C, also includes base component 34A generally including base component inferior surface 82A, opposing base component superior surface 84A, and base component peripheral wall 86A extending from inferior surface 82A to superior surface 84A. Base component 34A includes base anterior side 88A, base posterior side 90A, base lateral side 92A, and base medial side 94A.

Base component 34A includes protrusion 96A extending from superior surface 84A. Protrusion 96A includes nubs 104A which extend on opposing sides of protrusion 96A. Referring to FIG. 3B, protrusion bottom wall 100A spans the distance between protrusion 96A and superior surface 84A. Further, protrusion 96A and bottom wall 100A define bottom wall indentations 102A between protrusion 96A and superior surface 84A. Base component 34A also includes notch 106A at posterior side 90A having a generally W-shape, undercut portion 108A, medial side groove 110A, and lateral side groove 112A.

Figure 5:
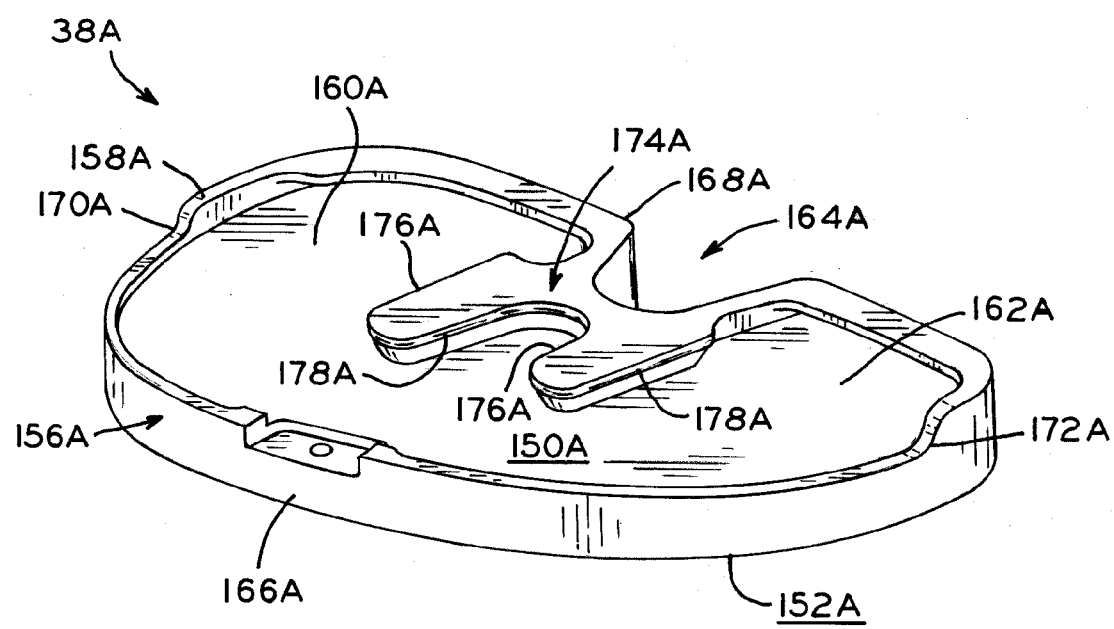
FIG. 5 is a perspective view of a tibial base plate of the provisional tibial prosthesis system of FIG. 1.

FIG. 5 illustrates tibial base plate 38A according to an exemplary embodiment of the present disclosure. Tibial base plate 38A generally includes base plate superior surface 150A and opposing base plate bone contacting surface 152A. Tibial base plate 38A closely corresponds in size and shape with the resected proximal tibia surface, and includes base plate peripheral wall 156A extending from bone contacting surface 152A to superior surface 150A. Base plate peripheral wall 156A includes raised perimeter 158A and tibial base plate 38A includes base plate anterior side 166A, base plate posterior side 168A, base plate medial side 170A, and base plate lateral side 172A. Superior surface 150A includes medial condylar portion 160A and lateral condylar portion 162A. Base plate 38A further includes PCL cut-out 164A disposed at posterior side 168A between medial condylar portion 160A and lateral condylar portion 162A to allow a posterior cruciate retaining ligament of a knee joint to pass therethrough. Further, tibial base plate 38A includes boss 174A having boss medial sides 176A and boss lateral sides 178A. Further, an interior recess is formed between inner medial side 176A and inner lateral side 178A.

The manner in which tibial base plate 38A is attached to a proximal tibia will now be discussed. The proximal portion of a patient's tibia is resected to provide a substantially flat surface for receipt of bone contacting surface 152A of tibial base plate 38A. Once the proximal tibia is resected, tibial base plate 38A is implanted and secured to the resected proximal tibia using standard surgical techniques. For example, conventional features such as a stem and fins may be located on bone contacting surface 152A to affect securement of tibial base plate 38A to a proximal tibia. While tibial base plate 38A is part of the provisional prosthesis system disclosed herein, tibial base plate 38A may also be part of a final prosthesis system, i.e., tibial base plate 38A is the final base plate implanted to a resected proximal tibia. Tibial base plate 38A may also be part of any other tibia contacting implement utilized in knee arthroplasty. For example, tibial base plate 38A could be part of a tibial sizing plate system in accordance with the tibial sizing plate described in U.S. Pat. No. 7,850, 698, issued Dec. 14, 2010, entitled "Tibial Trialing Assembly and Method of Trialing a Tibial Implant," the entire disclosure of which is hereby expressly incorporated herein by reference. Tibial base plate 38A may also be part of a tibial sizing plate system in accordance with the tibial sizing plate described in two brochures published by Zimmer, Inc., namely the "Zimmer® Patient Specific Instruments, Surgical Techniques for NexGen® Complete Knee Solution" brochure, copyright 2010, and the "Zimmer® NexGen Trabecular Metal Tibial Tray, Surgical Technique" brochure, copyright 2007 and 2009, the entire disclosures of which are hereby expressly incorporated herein by reference.

Figure 7:
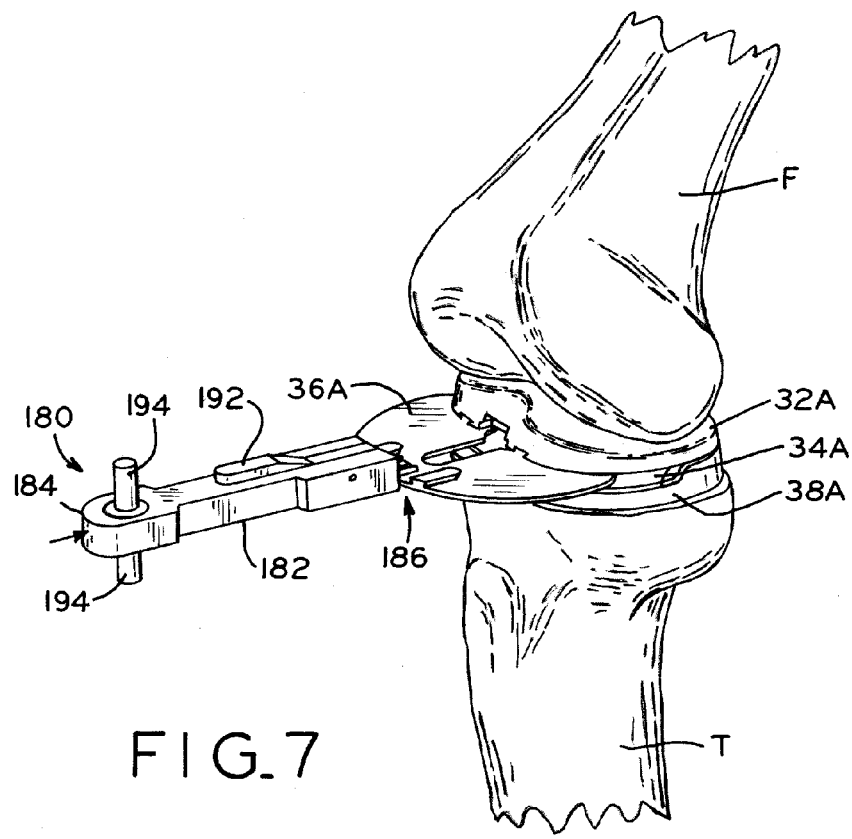
FIG. 7 is a perspective view of the provisional tibial prosthesis system of FIG. 6 illustrating using the surgical instrument of FIG. 6 to slide the shim between the base component and the tibial bearing component in an anterior/posterior direction.
Figure 8:
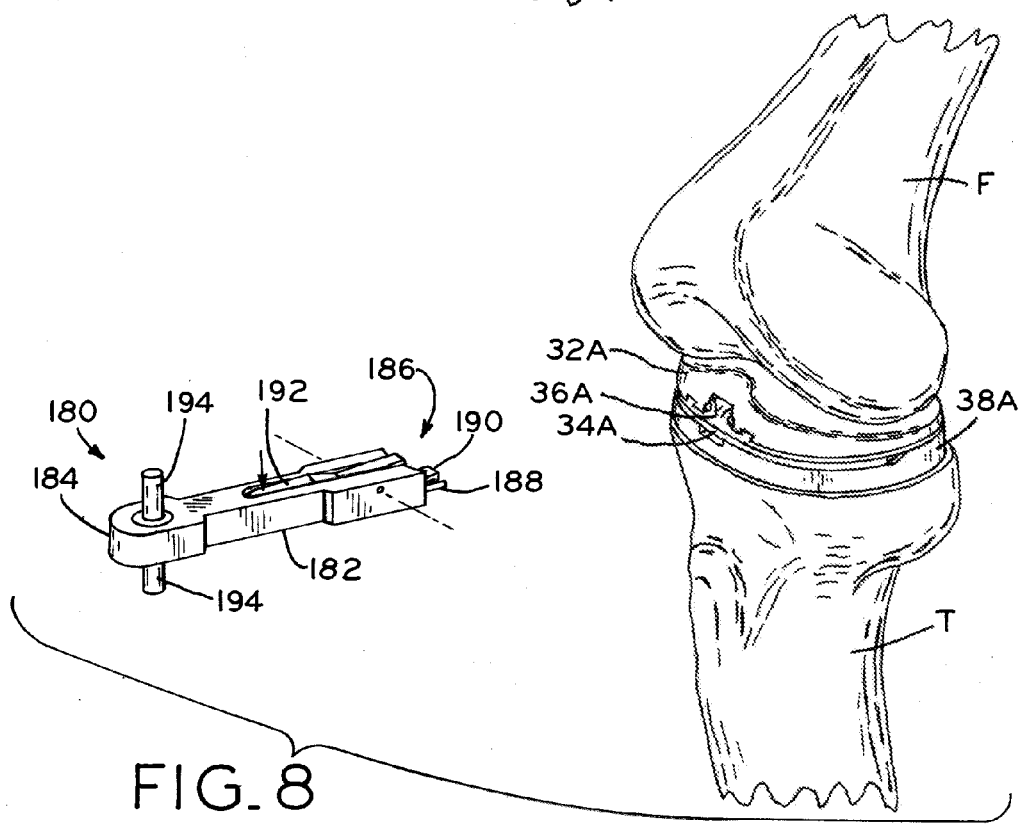
FIG. 8 is a perspective view of the provisional tibial prosthesis system of FIG. 6 illustrating the shim between the base component and the tibial bearing component.

In an exemplary embodiment, as illustrated in FIGS. 6-8, base component 34A is secured to tibial base plate 38A by positioning base component inferior surface 82A on base plate superior surface 150A. Undercut portion 108A (shown in FIGS. 3B and 3C) of base component 34A is positioned within raised perimeter 158A (shown in FIG. 5) of base plate peripheral wall 156A. Raised perimeter 158A acts as a physical barrier to prevent base component 34A from significant relative movement relative to tibial base plate 38A in medial/lateral direction 22 and anterior/posterior direction 20. In this embodiment, base component 34A is movable relative to tibial base plate 38A in proximal/distal direction 24. In one embodiment, base component 34A is sized to have clearance with tibial base plate 38A, i.e., some movement between base component 34A and tibial base plate 38A in medial/lateral direction 22 and anterior/posterior direction 20 is allowable, but base component 34A and tibial base plate 38A are prohibited from disengagement in medial/lateral direction 22 and anterior/posterior direction 20.

In another exemplary embodiment, tibial bearing component 32A is positioned atop tibial base plate 38A. In such an embodiment, bearing inferior surface 42A (shown in FIG. 2C) of bearing component 32A is positioned within raised perimeter 158A of base plate peripheral wall 156A in a manner similar to the attachment between base component 34A and tibial base plate 38A discussed above. Raised perimeter 158A again acts as a physical barrier to prevent bearing component 32A from significant relative movement relative to tibial base plate 38A in medial/lateral direction 22 and anterior/posterior direction 20. In this embodiment, bearing component 32A is movable relative to tibial base plate 38A in proximal/distal direction 24. In one embodiment, bearing component 32A is sized to have clearance with tibial base plate 38A, i.e., some movement between bearing component 32A and tibial base plate 38A in medial/lateral direction 22 and anterior/posterior direction 20 is allowable, but bearing component 32A and tibial base plate 38A are prohibited from disengagement in medial/lateral direction 22 and anterior/posterior direction 20.

Figure 9:
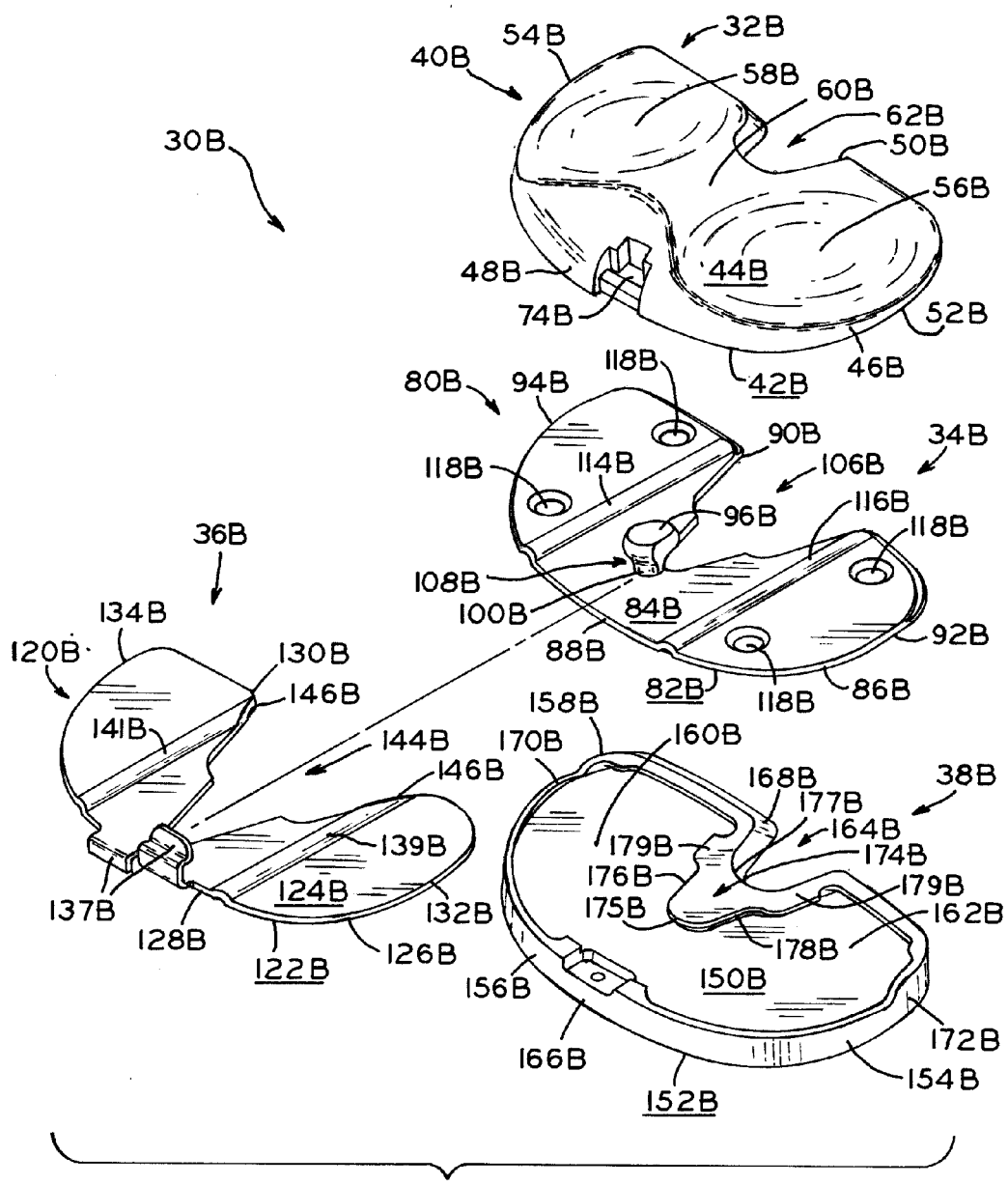
FIG. 9 is an exploded view of a provisional tibial prosthesis system in accordance with an exemplary second embodiment of the present disclosure.

For the purposes of this disclosure, any of the disclosed exemplary first through eleventh embodiments are attachable to a tibial base plate such as tibial base plates 38A, 38B respectively shown in FIGS. 5 and 9. It is also contemplated that other tibial base plates having a variety of different sizes and shapes can be used in accordance with the provisional tibial prosthesis systems of the present disclosure.

Referring to FIGS. 1-3C, the attachment of tibial bearing component 32A to base component 34A will now be described. Tibial bearing component 32A is positioned atop base component 34A by positioning protrusion 96A of base component 34A within bearing cavity 70A of tibial bearing component 32A and positioning nubs 104A of protrusion 96A respectively within bearing nub cavities 72A. In such an embodiment, base component 34A is locked to tibial bearing component 32A in medial/lateral direction 22 when protrusion 96A is received within bearing cavity 70A and base component 34A is locked to tibial bearing component 32A in anterior/posterior direction 20 when nubs 104A are respectively received within nub cavities 72A. The walls of bearing cavity 70A provide a physical barrier to prevent significant relative movement between base component 34A and tibial bearing component 32A in medial/lateral direction 22 and the walls of nub cavities 72A provide a physical barrier to prevent significant relative movement between base component 34A and tibial bearing component 32A in anterior/posterior direction 20. When tibial bearing component 32A is positioned atop base component 34A, tibial bearing component 32A is movable relative to base component 34A in proximal/distal direction 24. In this embodiment, as illustrated in FIGS. 6-8, base component 34A is secured to tibial base plate 38A and base component 34A is located between tibial bearing component 32A and tibial base plate 38A. In another embodiment, as discussed above, tibial bearing component 32A can be positioned directly atop tibial base plate 38A.

Figure 4A:
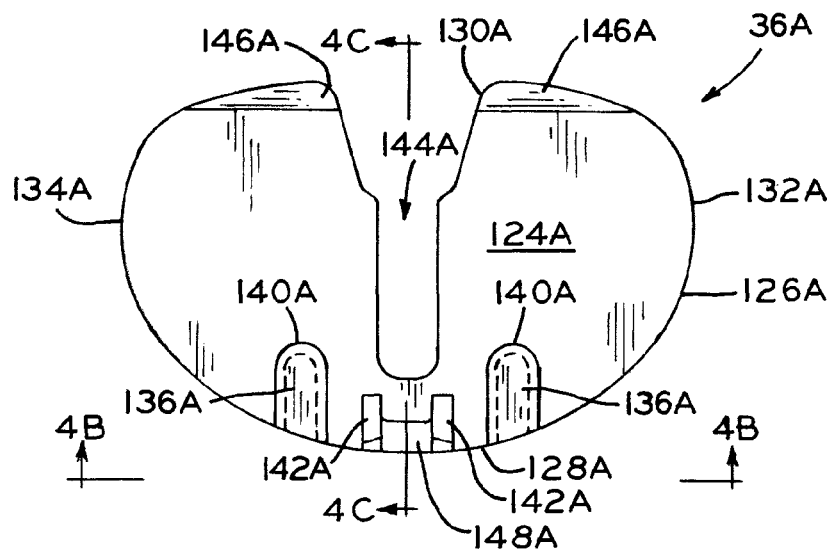
FIG. 4A is a plan view of a shim of the provisional tibial prosthesis system of FIG. 1.
Figure 4B:
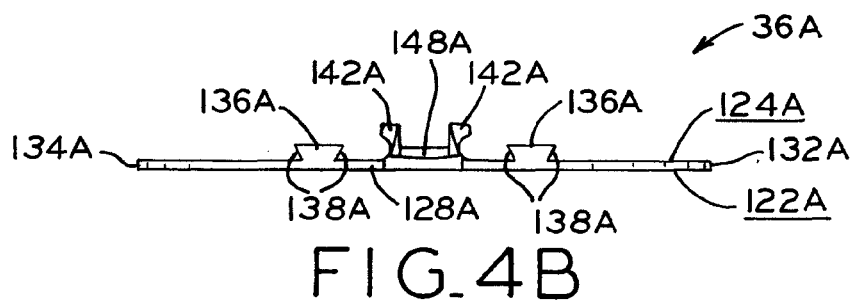
FIG. 4B is a front elevation view of the shim of FIG. 4A.
Figure 4C:
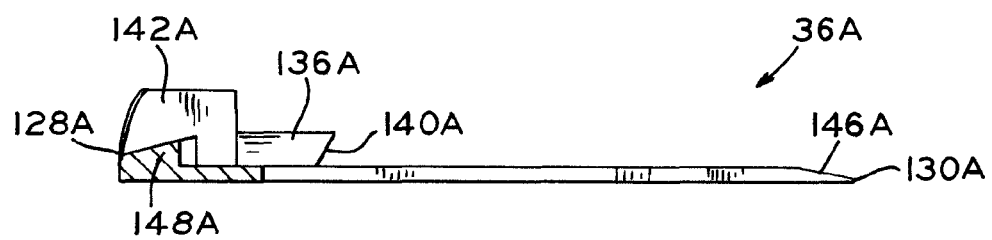
FIG. 4C is a cross-sectional view taken along line 4C-4C of FIG. 4A.

FIGS. 4A-4C illustrate shim 36A according to an exemplary embodiment of the present disclosure. Shim 36A generally includes shim inferior surface 122A, opposing shim superior surface 124A, and shim peripheral wall 126A extending from inferior surface 122A to superior surface 124A. Shim peripheral wall 126A defines a shim exterior profile. In one embodiment, the shim exterior profile substantially matches the tibial base plate exterior profile. Shim 36A also includes shim anterior side 128A, shim posterior side 130A, shim lateral side 132A, and shim medial side 134A. As shown in FIGS. 4A-4C, shim superior surface 124A includes rails 136A and handle alignment rails 142A. As illustrated in FIGS. 4A and 4B, rails 136A extend from anterior side 128A toward posterior side 130A parallel to anterior/posterior axis $A_{A-P}$ (shown in FIG. 6). In an exemplary embodiment, rails 136A have lead-in edges 140A and tapered walls 138A. Handle alignment rails 142A are located between rails 136A at anterior side 128A. Further, between handle alignment rails 142A is shim ramp 148A. Shim 36A also includes shim notch 144A and lead-in walls 146A, i.e., tapering posterior walls, at posterior side 130A for aligning shim 36A and guiding insertion of shim 36A in anterior/posterior direction 20, as will be further described below.

In an exemplary embodiment, a set of a plurality of shims 36A can be provided to allow for varying levels of adjustment of provisional tibial prosthesis system 30A, i.e., increasing the distance between tibial bearing component 32A and base component 34A by the shim height of a particular shim 36A inserted therebetween. For example, if four different sizes were to be used in the set of shims, the height of the shims could be 1 mm, 2 mm, 3 mm, and 4 mm. In another embodiment, a set of shims could include a plurality of shims having equal sizes for stacking shims. The stacking shims embodiment can also include a plurality of shims having varying heights. It is envisioned that the set of a plurality of different sized shims 36A could include any desired number of different sized shims having any number of shim heights.

During insertion of shim 36A, as best shown in FIGS. 6 and 7, lead-in walls 146A of shim 36A are placed between bearing component 32A and base component 34A and are used to affect separation of bearing component 32A from base component 34A by a distance along proximal/distal axis $A_{P-D}$ equal to a height of shim 36A. In this manner, lead-in walls 146A act as a ramp to separate bearing component 32A from base component 34A. Advantageously, the provisional tibial prosthesis system of the present disclosure can be adjusted in a manner requiring the knee joint to only be distracted by a distance equal to the height of shim 36A. In another embodiment, to further help separation of bearing component 32A from base component 34A, bearing component inferior surface 42A (shown in FIG. 2C) at bearing anterior side 48A (shown in FIGS. 2A-2C) can include a beveled edge corresponding to lead-in walls 146A of shim 36A.

As illustrated in FIGS. 6-8, in one exemplary embodiment, shim 36A is slidably receivable between tibial bearing component 32A and base component 34A in anterior/posterior direction 20. The insertion of shim 36A between tibial bearing component 32A and base component 34A in anterior/posterior direction 20 allows tibial bearing component 32A to only be separated from base component 34A by a distance along proximal/distal axis $A_{P-D}$ equal to the height of shim 36A. Also, tibial bearing component 32A and base component 34A of provisional tibial prosthesis system 30A do not have to be removed from the knee joint to insert and remove shims 36A.

In an alternative embodiment, base component 34A is not utilized and shim 36A is positioned between bearing component 32A and base plate 38A. In this embodiment, tibial bearing component 32A is positioned atop tibial base plate 38A such that bearing inferior surface 42A (shown in FIG. 2C) of bearing component 32A is positioned within raised perimeter 158A of base plate peripheral wall 156A. Referring to FIG. 5, in such an embodiment, the anterior rail of base plate 38A will be missing to allow shim 36A to be slidably receivable between tibial bearing component 32A and tibial base plate 38A in anterior/posterior direction 20 using lead-in walls 146A of shim 36A to separate tibial bearing component 32A from tibial base plate 38A by a distance along proximal/distal axis $A_{P-D}$ equal to a height of shim 36A. In this embodiment, shim 36A will have a perimeter configured to allow shim 36A to be positioned to the securement features of base plate 38A. For example, shim 36A will have a perimeter similar to the perimeter of base component 34A (shown in FIG. 3A).

As previously discussed, when tibial bearing component 32A is positioned atop base component 34A, tibial bearing component 32A is movable relative to base component 34A in proximal/distal direction 24. In the exemplary first embodiment, shim 36A takes away this last degree of freedom between tibial bearing component 32A and base component 34A, i.e., when shim 36A is received between base component 34A and tibial bearing component 32A, shim 36A locks tibial bearing component 32A to base component 34A in proximal/distal direction 24, i.e., significant relative movement between tibial bearing component 32A and base component 34A in proximal/distal direction 24 is prevented.

The manner in which shim 36A locks tibial bearing component 32A to base component 34A in proximal/distal direction 24 will now be discussed. Referring to FIGS. 6-8, shim 36A is inserted between tibial bearing component 32A and base component 34A in anterior/posterior direction 20. Referring to FIGS. 2A-2D and 4A-4C, and 6, shim rails 136A are aligned with respective tibial bearing component slots 64A. Referring to FIG. 4A, rails 136A each include lead-in edge 140A to guide insertion of rails 136A in slots 64A. The rail/slot connection between shim 36A and tibial bearing component 32A is important because it prevents lift-off of tibial bearing component 32A from shim 36A, i.e., prevents significant relative movement between tibial bearing component 32A and shim 36A in proximal/distal direction 24. In one exemplary embodiment, as shown in FIGS. 2A-2D and 4A-4C, slots 64A of tibial bearing component 32A and rails 136A of shim 36A each have a dovetail cross-sectional shape. Slots 64A including tapering walls 66A of bearing component 32A cooperate with rails 136A having tapering walls 138A of shim 36A to act as a physical barrier to prevent lift-off of the tibial bearing component 32A from shim 36A. In an alternate embodiment, slots 64A of tibial bearing component 32A and rails 136A of shim 36A can each have a T-shaped cross-sectional shape or other various shapes that would provide a physical barrier that would prevent lift-off, i.e., prevent significant relative movement between tibial bearing component 32A and base component 34A in proximal/distal direction 24, or any movement of tibial bearing component 32A in any direction that is perpendicular to base component 34A.

Referring to FIGS. 3A-4C, as shim 36A is inserted in anterior/posterior direction 20 between tibial bearing component 32A and base component 34A using lead-in walls 146A as discussed above, shim 36A also locks to base component 34A by shim notch 144A formed in shim posterior side 130A attaching to base component 34A by sliding notch 144A in indentations 102A between protrusion 96A and base component superior surface 84A. This shim connection between shim 36A and base component 34A and the rail/slot connection between shim 36A and tibial bearing component 32A allows shim 36A to lock tibial bearing component 32A to base component 34A in proximal/distal direction 24.

Referring to FIGS. 19A-19E, an alternate embodiment including tibial bearing component 32L and shim 36L is illustrated. Tibial bearing component 32L and shim 36L respectively include similar components to tibial bearing component 32A illustrated in FIGS. 2A-2D and shim 36A illustrated in FIGS. 4A-4C. For the sake of brevity, these similar components will not all be discussed in conjunction with the alternate embodiments disclosed in FIGS. 19A-19E. Referring to FIGS. 19A and 19B, tibial bearing component 32L includes recess 78L extending from bearing component inferior surface 42L towards bearing component superior surface 44L. Recess 78L is sized to receive shim 36L (shown in FIGS. 19C and 19D). FIG. 19E illustrates shim 36L received in recess 78L of tibial bearing component 32L. Referring to FIGS. 19A and 19C, shim rails 136L are aligned with respective tibial component slots 64L. Rails 136L of shim 36L each include lead-in edge 140L to guide insertion of rails 136L in slots 64L of tibial bearing component 32L. Shim 36L is inserted in recess 78L of tibial bearing component 32L in anterior/posterior direction 20 (shown in FIG. 6). In one embodiment, the height of shim 36L is equal to the height of recess 78L of tibial bearing component 32L. In other embodiments, the height of shim 36L could be less than the height of recess 78L. In this embodiment, shim 36L locks tibial bearing component 32L to shim 36L in proximal/distal direction 24 (shown in FIG. 6) without spacing tibial bearing component 32L from a base component, i.e., either base component 34A (shown in FIGS. 3A-3C), tibial base plate 38A (shown in FIG. 5), or other tibia contacting implement utilized in knee arthroplasty.

Before shim 36L is inserted between tibial bearing component 32L and base component 34A (shown in FIGS. 3A-3C), tibial bearing component 32L is positioned on base component 34A. With tibial bearing component 32L positioned on base component 34A, recess 78L spaces tibial bearing component 32L from base component 34A a distance along proximal/distal axis $A_{P-D}$ (shown in FIG. 6) at least equal to the height of shim 36L. Referring to FIGS. 3A-3C, 19A and 19E, in one embodiment, tibial bearing component 32L can be positioned on base component 34A by positioning protrusion 96A of base component 34A within bearing cavity 70L of tibial bearing component 32L and positioning nubs 104A of protrusion 96A respectively within bearing nub cavities 72L. Subsequently, shim 36L can be inserted between tibial bearing component 32L and base component 34A in anterior/posterior direction 20 (shown in FIG. 6). With shim 36L inserted within recess 78L of tibial bearing component 32L, shim 36L prevents significant relative movement between tibial bearing component 32L and base component 34A in proximal/distal direction 24 (shown in FIG. 6) without spacing tibial bearing component 32L from base component 34A. Referring to FIGS. 19B and 19E, because shim 36L is received in recess 78L of tibial bearing component 32L, the height of shim 36L cooperates with the height of tibial bearing component 32L to represent a first final tibial prosthesis without shim 36L adding to the height of tibial bearing component 32L.

Referring to FIGS. 6-8, an illustrative procedure in accordance with the present disclosure to determine the size of a final tibial prosthesis for a prosthetic knee joint for implantation in a natural knee will now be described. In one embodiment, a surgeon selects a provisional tibial prosthesis system, such as provisional tibial prosthesis system 30A, having tibial base plate 38A (shown in FIG. 5) having bone contacting surface 152A and opposing base plate superior surface 150A, tibial bearing component 32A having a tibial bearing component height, tibial bearing component 32A attachable to tibial base plate 38A, and shim 36A having a shim height, shim 36A slidably receivable between tibial base plate 38A and tibial bearing component 32A in anterior/posterior direction 20 when tibial base plate 38A and tibial bearing component 32A are separated by a distance along proximal/distal axis $A_{P-D}$ equal to the shim height.

Next, the proximal portion of a patient's tibia is resected using standard surgical techniques to provide a substantially flat surface for receipt of bone contacting surface 152A of tibial base plate 38A. Once the proximal tibia is resected, tibial base plate 38A is implanted and secured to the resected proximal tibia. Subsequently, tibial bearing component 32A corresponding to the constraint level chosen by the surgeon is positioned atop tibial base plate 38A such that bearing inferior surface 42A (shown in FIG. 2C) of bearing component 32A is positioned within raised perimeter 158A (shown in FIG. 5) of base plate peripheral wall 156A. If base component 34A is utilized, base component 34A is positioned atop tibial base plate 38A between bearing component 32A and base plate 38A.

The surgeon can then perform range of motion testing of the knee joint to verify proper sizing of the provisional tibial prosthesis system. If a surgeon determines that a provisional tibial prosthesis system is properly sized with tibial bearing component 32A positioned atop tibial base plate 38A, a first final tibial prosthesis can be selected which corresponds to the height of tibial bearing component 32A. If the provisional tibial prosthesis system is determined to not be properly sized, tibial bearing component 32A can be spaced from tibial base plate 38A by sliding shim 36A having a first shim height, e.g., 1 mm, between tibial base plate 38A and tibial bearing component 32A in anterior/posterior direction 20.

The surgeon can then perform range of motion testing of the knee joint to verify proper sizing of the provisional tibial prosthesis system with shim 36A having a first shim height inserted between tibial bearing component 32A and tibial base plate 38A. If the provisional tibial prosthesis system is determined by the surgeon to be properly sized with shim 36A having first shim height between bearing component 32A and tibial base plate 38A, the surgeon can select a second final tibial prosthesis represented by the first shim height and the tibial bearing component height.

In one embodiment, if the provisional tibial prosthesis system is not properly sized after insertion of shim 36A having the first shim height, e.g., 1 mm, the 1 mm shim 36A can be removed in anterior/posterior direction 20, another shim 36A may be selected having a second height, e.g., 2 mm, and tibial bearing component 32A can then be spaced from tibial base plate 38A by sliding shim 36A having the second shim height between tibial base plate 38A and tibial bearing component 32A in anterior/posterior direction 20. If the provisional tibial prosthesis system is determined by the surgeon to be properly sized with shim 36A having second shim height, e.g., 2 mm, the surgeon can select a third final tibial prosthesis represented by the second shim height and the tibial bearing component height.

In an alternate embodiment, after inserting shim 36A having a first shim height, e.g., 1 mm, if a surgeon determines that the provisional tibial prosthesis system with shim 36A having the first shim height is not properly sized, shim 36A having a height of 1 mm can be left between tibial base plate 38A and tibial bearing component 32A, and a second shim 36A having a second shim height, e.g., 1 mm, can be inserted in anterior/posterior direction 20 between tibial base plate 38A and tibial bearing component 32A to separate tibial bearing component 32A from tibial base plate 38A by a distance along proximal/distal axis $A_{P-D}$ equal to the first shim height and the second shim height. In this embodiment, shim 36A may not include either the securement features discussed above that lock shim 36A to tibial bearing component 32A or the securement features discussed above that lock shim 36A to base component 34A. For example, referring to FIGS. 4A and 4B, shim 36A may not include rails 136A so that tibial bearing component 32A can move relative to shim 36A in proximal/distal direction 24 (shown in FIG. 6) when shim 36A is inserted between base plate 38A and bearing component 32A. In this manner, a second shim can be inserted in anterior/posterior direction 20 between base plate 38A and bearing component 32A with a first shim already positioned between base plate 38A and bearing component 32A.

If the provisional prosthesis system is determined by the surgeon to be properly sized with both shims 36A inserted, the surgeon can select a third final tibial prosthesis represented by the first shim height, the second shim height, and the tibial bearing component height. This stacking of the shims can be repeated using a variety of different sized shims and a variety of different numbered shims for a surgeon to determine the proper thickness of a provisional tibial prosthesis system. In an alternative embodiment, several shims all having the same height can be used in series to adjust the spacing of bearing component 32A from base plate 38A.

Referring to FIGS. 6-8, the use of surgical instrument 180 to insert shim 36A will now be described. FIGS. 6-8 illustrate surgical instrument 180 for insertion or removal of shim 36A. Surgical instrument 180 generally includes handle body 182, handle end 184, opposing attachment end 186, alignment pins 188, tooth 190, button 192, and handle pegs 194. Surgical instrument 180 has one alignment pin 188 on each side of tooth 190. Alignment pins 188 fit in respective exterior circular recesses in rails 142A (shown in FIG. 4B) of shim 36A to properly align surgical instrument 180 to shim 36A. Once properly aligned, tooth 190 of surgical instrument 180 slides along shim ramp 148A (shown in FIGS. 4A and 4B) and, when tooth 190 slides past shim ramp 148A, a biasing force on tooth 190 causes tooth 190 to travel downward and engage the backside of shim ramp 148A to lock surgical instrument 180 to shim 36A. In one embodiment, a biasing force is exerted on tooth 190 by a tension spring. When surgical instrument 180 is properly locked to shim 36A, a surgeon holding handle end 184 of surgical instrument 180 can insert shim 36A in anterior/posterior direction 20 between tibial bearing component 32A and tibial base plate 38A to space tibial bearing component 32A from tibial base plate 38A along proximal/distal axis $A_{P-D}$ a distance equal to the shim height. Once shim 36A is properly inserted between tibial bearing component 32A and tibial base plate 38A, release button 192 of surgical instrument 180 can be depressed to overcome the biasing force of the spring to release and disengage tooth 190 from the backside of shim ramp 148A. Thereafter, surgical instrument 180 can be removed. In another embodiment, surgical instrument 180 can be used in the manner described above to insert shim 36A in anterior/posterior direction 20 between tibial bearing component 32A and base component 34A. Also, surgical instrument 180 may be used to remove shim 36A from between tibial bearing component 32A and base component 34A.

Once the proximal portion of a patient's tibia is resected and the tibial prosthesis components of the present disclosure are secured to the resected proximal tibia, soft tissue balancing of the knee can be performed. Subsequently, a sizing guide can be attached to the tibial prosthesis components. Similar to the attachment of surgical instrument 180 to shim 36A, the sizing guide can include alignment pins that fit in respective exterior circular recesses in rails 142A (shown in FIG. 4B) of shim 36A to properly align the sizing guide to shim 36A. Once properly aligned, a locking component of the sizing guide can slide along shim ramp 148A (shown in FIGS. 4A and 4B) and, when the locking component slides past shim ramp 148A, a biasing force on the locking component can cause the locking component to travel downward and engage the backside of shim ramp 148A to lock the sizing guide to shim 36A. Similarly, a cut guide such as a femoral finishing cut guide can be attached to shim 36A.

FIG. 9 illustrates an exemplary second embodiment. The several embodiments of the present disclosure include similar components to the embodiment illustrated in FIGS. 1-8. For the sake of brevity, these similar components will not all be discussed in conjunction with the various alternative embodiments disclosed herein. Exemplary second embodiment provisional tibial prosthesis system 30B includes tibial bearing component 32B, base component 34B, shim component 36B, and tibial base plate 38B. In one embodiment, tibial bearing component 32B is positioned atop base component 34B in a manner similar to the arrangement of tibial bearing component 32A to base component 34A discussed above. For example, protrusion 96B is similar to protrusion 96A (shown in FIGS. 3A-3C), and bearing cavity 70A (shown in FIGS. 2C and 2D) is similar to a cavity (not shown) in bearing component inferior surface 42B. Similar to the arrangement of protrusion 96A of base component 34A and bearing cavity 70A of bearing component 32A, bearing component 32B is positioned atop base component 34B by positioning protrusion 96B of base component 34B within a bearing cavity in inferior surface 42B of bearing component 32B to lock bearing component 32B to base component 34B in medial/lateral direction 22 and anterior/posterior direction 20. Similar to the exemplary first embodiment, shim 36B is slidably receivable between tibial bearing component 32B and base component 34B in anterior/posterior direction 20. As in the exemplary first embodiment, a set of different sized shims 36B can be provided to allow for varying levels of adjustment of provisional tibial prosthesis system 30B, i.e., increasing the distance between tibial bearing component 32B and base component 34B by the shim height of a particular shim 36B inserted therebetween.

Referring to FIG. 9, shim superior surface 124B includes lateral alignment bump 139B and medial alignment bump 141B which respectively cooperate with lateral alignment bump 116B and medial alignment bump 114B of base component 34B to align shim 36B and guide insertion of shim 36B in anterior/posterior direction 20. During insertion of shim 36B, alignment bumps 139B, 141B are placed between bearing component 32B and respective alignment bumps 114B, 116B of base component 34B and are used to affect separation of bearing component 32B from base component 34B by a distance along proximal/distal axis $A_{P-D}$ equal to a height of shim 36B. Alignment bumps 139B, 141B of shim 36B and alignment bumps 114B, 116B of base component 34B each include a protrusion portion on a proximal side and a recessed portion on a distal side.

In one embodiment, the insertion end of shim 36B could include lead-in walls similar to lead-in walls 146A (shown in FIGS. 4A and 4C) to act as a ramp to separate bearing component 32B from base component 34B. Further, every embodiment of the present disclosure including a shim component slidably insertable between a bearing component and a bearing support could include an insertion end having a lead-in wall to act as a ramp to separate the bearing component from the bearing support.

Instead of the rail/slot connection system of the first exemplary embodiment, in the exemplary second embodiment, shim 36B includes locking tabs 137B located at shim anterior side 128B. Upon insertion of shim 36B between tibial bearing component 32B and base component 34B, shim 36B respectively locks shim 36B to tibial bearing component 32B by a first tab 137B engaging in notch 74B of tibial bearing component 32B and locks shim 36B to base component 34B by a second tab 137B engaging base component 34B at anterior side 88B. In this manner, shim 36B takes away the last degree of freedom between tibial bearing component 32B and base component 34B, i.e., when shim 36B is received between base component 34B and tibial bearing component 32B, shim 36B limits movement between tibial bearing component 32B and base component 34B in proximal/distal direction 24. In such an embodiment, a surgeon can grasp tabs 137B to insert or remove shim 36B from bearing component 32B and base component 34B. Alternatively, a surgeon can use a standard surgical instrument for insertion or removal of shim 36B.

In an alternative embodiment, base component 34B is not utilized and shim 36B is positioned between bearing component 32B and base plate 38B. Referring to FIG. 9, in such an embodiment, the anterior rail of base plate 38B will be missing to allow shim 36B to be slidably receivable between tibial base plate 38B and tibial bearing component 32B in anterior/posterior direction 20.

In another embodiment, after inserting shim 36B having a first shim height, e.g., 1 mm, if a surgeon determines that the provisional tibial prosthesis system with shim 36B having the first shim height is not properly sized, shim 36B having a height of 1 mm can be left between base plate 38B and tibial bearing component 32B, and a second shim having a second shim height, e.g., 1 mm, can be inserted between base plate 38B and bearing component 32B to separate bearing component 32B from base plate 38B by a distance along proximal/distal axis $A_{P-D}$ equal to the first shim height and the second shim height. In this embodiment, shim 36B will not include tabs 137B so that bearing component 32B can move relative to shim 36B in proximal/distal direction 24 (shown in FIG. 6) when shim 36B is inserted between base plate 38B and bearing component 32B. In this manner, a second shim can be inserted in anterior/posterior direction 20 between base plate 38B and bearing component 32B with a first shim already positioned between base plate 38B and bearing component 32B. In the embodiment including shim 36B with no tabs 137B, a standard surgical instrument such as forceps can be used for insertion or removal of shim 36B from bearing component 32B and base component 34B.

Referring to FIG. 9, base component 34B includes apertures 118B. As illustrated in FIG. 9, two apertures 118B are located near lateral portion 92B and two apertures 118B are located near medial portion 94B. Apertures 118B could receive pegs (not shown) extending from base plate superior surface 150B to allow base plate 38B to snap fit together with base component 34B. Base plate 38B includes boss 174B having boss anterior side 175B, boss medial side 176B, boss posterior side 177B, boss lateral side 178B, and boss winged portions 179B.

Figure 10A:
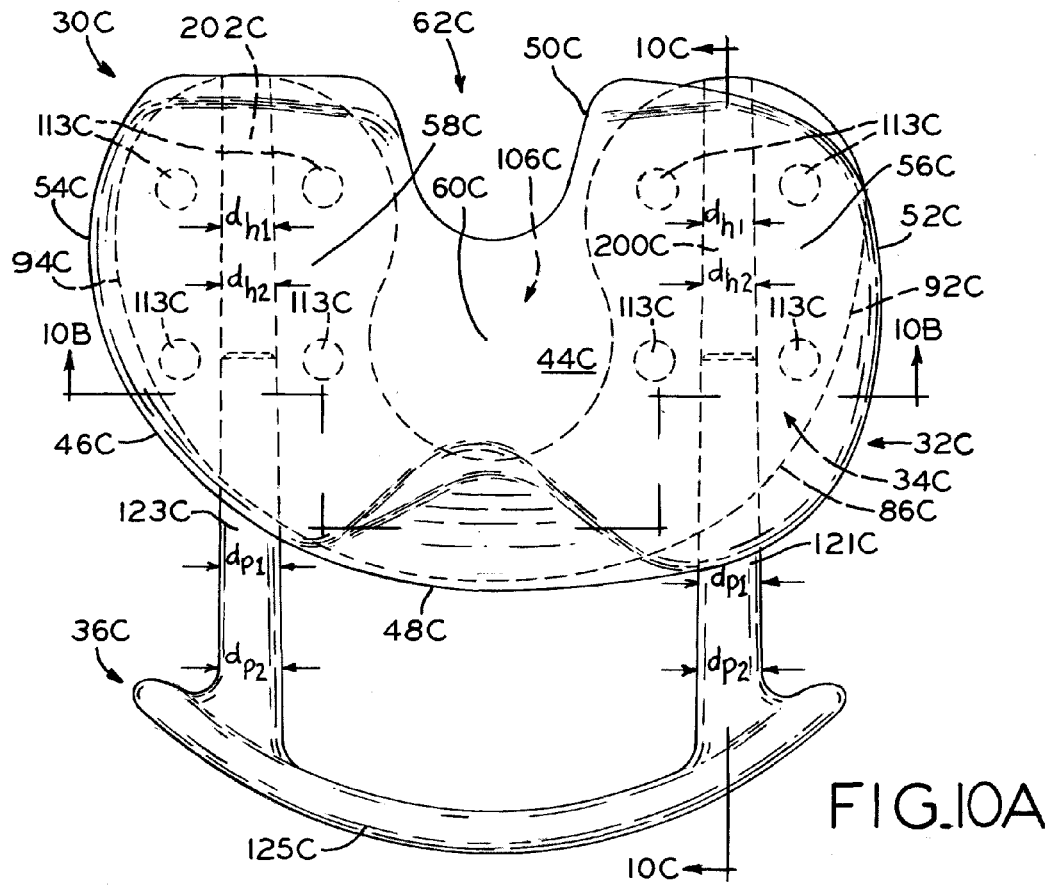
FIG. 10A is a plan view of a provisional tibial prosthesis system in accordance with an exemplary third embodiment of the present disclosure.
Figure 10B:
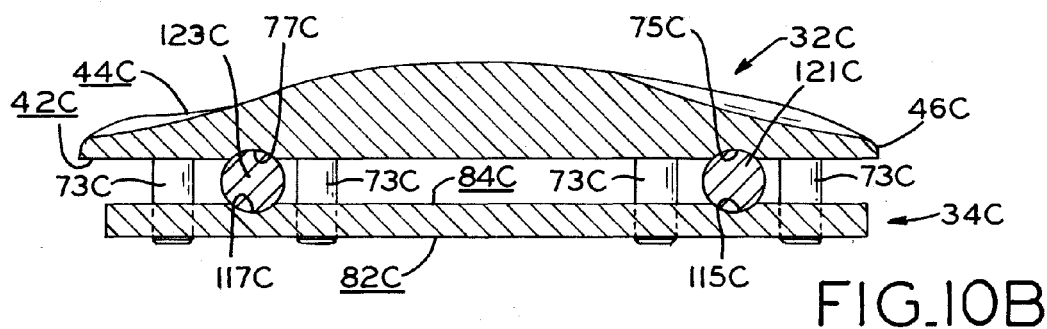
FIG. 10B is a cross-sectional view taken along line 10B-10B of FIG. 10A.
Figure 10C:
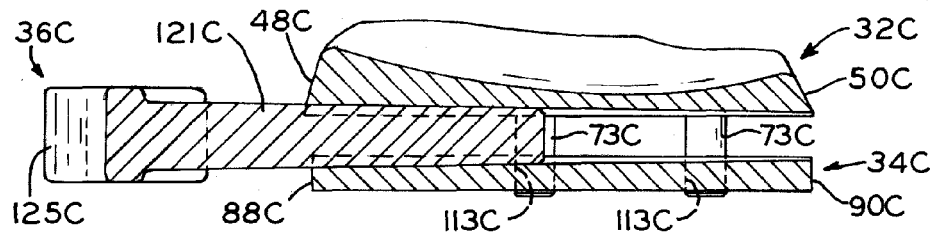
FIG. 10C is a cross-sectional view taken along line 10C-10C of FIG. 10A.

FIGS. 10A-10C illustrate an exemplary third embodiment. Exemplary third embodiment provisional tibial prosthesis system 30C includes tibial bearing component 32C, base component 34C, and pin shim component 36C having lateral pin 121C, medial pin 123C, and handle 125C. Tibial bearing component inferior surface 42C includes eight posts 73C extending in a distal direction therefrom. For example, four posts 73C are located beneath medial articular surface 58C and four posts 73C extend beneath lateral articular surface 56C. Referring to FIG. 10A, base component 34C includes eight apertures 113C extending through base component 34C from inferior surface 82C to superior surface 84C. For example, four apertures 113C are located in medial portion 94C and four apertures 113C are located in lateral portion 92C. Each aperture 113C receives a single post 73C of tibial bearing component 32C therein to secure tibial bearing component 32C to base component 34C. In the exemplary embodiment, corresponding posts 73C and apertures 113C lock tibial bearing component 32C to base component 34C in medial/lateral direction 22 and anterior/posterior direction 20. In such an embodiment, tibial bearing component 32C is moveable relative to base component 34C in proximal/distal direction 24. However, when provisional tibial prosthesis system 30C is positioned in a knee joint, the knee joint will exert forces in proximal/distal direction 24 to keep tibial bearing component 32C from pulling off base component 34C.

Referring to FIG. 10B, tibial bearing component inferior surface 42C includes curved lateral groove 75C and curved medial groove 77C therein, and base component superior surface 84C includes curved lateral groove 115C and curved medial groove 117C therein. Lateral groove 75C and lateral groove 115C correspond to form first mating hole portion 200C and medial groove 77C and medial groove 117C correspond to form second mating hole portion 202C. Referring to FIG. 10A, mating hole portion 200C receives pin 121C therein and mating hole portion 202C receives pin 123C therein.

Referring to FIGS. 10A-10C, the use of pin shim 36C to change the thickness of provisional tibial prosthesis system 30C, i.e., the distance between tibial bearing component 32C and base component 34C, will now be described. As shown in FIG. 10A, pins 121C, 123C are slidably received between base component 34C and tibial bearing component 32C, within respective mating hole portions 200C, 202C, in anterior/posterior direction 20. In an exemplary embodiment, mating hole portions 200C, 202C each have a variable mating hole diameter $dh_1$, $dh_2$. In such an embodiment, referring to FIG. 10A, the diameters of mating hole portions 200C, 202C decrease from anterior side 48C to posterior side 50C. For example, mating hole diameter $dh_2$ is greater than mating hole diameter $dh_1$. In this embodiment, the diameter of pins 121C, 123C are equal, i.e., pin diameter $dp_1$ is equal to pin diameter $dp_2$. Accordingly, because mating hole diameters $dh_1$, $dh_2$ decrease towards posterior side 50C, the further pin shim 36C is slid within mating hole portions 200C, 202C, the distance between tibial bearing component 32C and base component 34C is increased.

In another exemplary embodiment, referring to FIG. 10A, the diameter of pins 121C, 123C vary and mating hole diameters $dh_1$, $dh_2$ of mating hole portions 200C, 202C remain the same. For example, in such an embodiment, pin diameter $dp_2$ is greater than pin diameter $dp_1$ for both pins 121C and 123C. Further, mating hole diameter $dh_1$ and $dh_2$ are equal throughout mating hole portions 200C, 202C. In such an embodiment, because the pin diameters of pins 121C, 123C increase in a direction towards handle 125C, the further pin shim 36C is slid within mating hole portions 200C, 202C, the distance between tibial bearing component 32C and base component 34C is increased.

In another exemplary embodiment, both pin diameters $dp_1$, $dp_2$ of pins 121C, 123C and mating hole diameters $dh_1$, $dh_2$ of mating hole portions 200C, 202C vary. For example, in such an embodiment, pin diameter $dp_2$ is greater than pin diameter $dp_1$ for both pins 121C and 123C and mating hole diameter $dh_2$ is greater than mating hole diameter $dh_1$ for both mating hole portions 200C, 202C. Such an embodiment allows for the greatest thickness adjustment because not only does the mating hole diameters decrease towards posterior side 50C, the pin diameters increase towards handle 125C. As in the previous two exemplary embodiments, the further pin shim 36C is slid within mating hole portions 200C, 202C, the distance between tibial bearing component 32C and base component 34C is increased.

In an exemplary embodiment, a set of different sized pin shims 36C can be provided to allow for varying levels of adjustment of provisional tibial prosthesis system 30C, i.e., increasing the distance between tibial bearing component 32C and base component 34C by the diameters of pins 121C, 123C. It is envisioned that the set of different sized pin shims 36C could include any desired number of different sized pin shims 36C having any number of different pin diameters.

FIGS. 11A and 11B illustrate an exemplary fourth embodiment. Exemplary fourth embodiment provisional tibial prosthesis system 30D includes tibial bearing component 32D, base component 34D, and sliding wedge 36D. Base component superior surface 84D includes base component medial alignment bump 114D and base component lateral alignment bump 116D. Tibial bearing component 32D is positioned on base component 34D such that bearing inferior surface 42D is adjacent to base component superior surface 84D as illustrated in FIG. 11B.

Sliding wedge 36D is generally U-shaped and includes tab 137D, lateral alignment bump 139D, medial alignment bump 141D, lateral wing 143D, anterior wedge portion 144D, and medial wing 145D. As illustrated in FIG. 11A, lateral wing 143D and medial wing 145D each include lead-in edge 140D, which function similarly to lead-in walls 146A as discussed above. Anterior wedge portion 144D includes lateral wing 143D and medial wing 145D extending at opposing sides of anterior wedge portion 144D. Further, tab 137D extends from anterior wedge portion 144D. In an exemplary embodiment, indicia of a particular sized thickness of sliding wedge 36D can be included on tab 137D.

Sliding wedge 36D can be provided in a variety of different thicknesses to provide for varying levels of adjustment of provisional tibial prosthesis system 30D, i.e., increasing the distance between tibial bearing component 32D and base component 34D. For example, if four different sizes were to be used in the set of sliding wedges 36D, the height of sliding wedges 36D could be 1 mm, 2 mm, 3 mm, and 4 mm. It is envisioned that the set of different sized sliding wedges 36D could include any desired number of different sized wedges 36D having any number of different wedge heights.

Referring to FIGS. 11A and 11B, the use of sliding wedge 36D to change the thickness of provisional tibial prosthesis system 30D, i.e., the distance between tibial bearing component 32D and base component 34D, will now be described. In use, sliding wedge lateral alignment bump 139D and sliding wedge medial alignment bump 141D are respectively aligned with base component lateral alignment bump 116D and base component medial alignment bump 114D to properly orientate sliding wedge 36D between tibial bearing component 32D and base component 34D. Once properly aligned, lead-in edges 140D of sliding wedge 36D are placed between tibial bearing component 32D and base component 34D to effect separation of bearing component 32D from base component 34D and wedge 36D is slidably inserted between base component 34D and tibial bearing component 32D in anterior/ posterior direction 20. Alignment bumps 139B, 141D of sliding wedge 36D include a protrusion portion on a proximal side and a recessed portion on a distal side.

The shims of the present disclosure can be made of a surgical grade material such as stainless steel, various alloys such as a cobalt-chromium alloy, and various ceramics such as silicon nitride. The shims can also be made of various plastics including polyethylene and polyphenylsulfone. In certain embodiments, the shims of the present disclosure will be disposable after a single use.

Figure 12A:
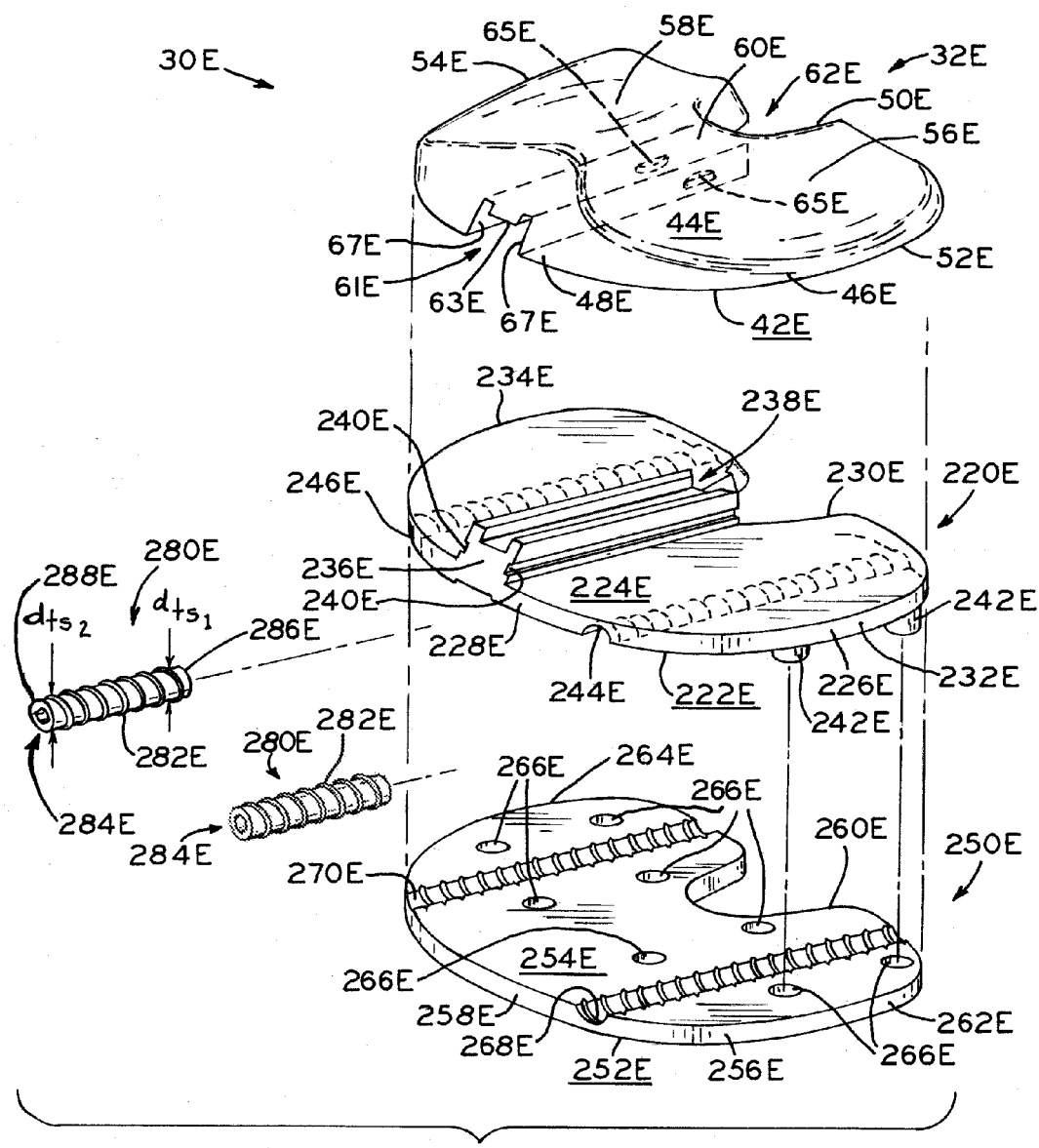
FIG. 12A is an exploded view of a provisional tibial prosthesis system in accordance with an exemplary fifth embodiment of the present disclosure.
Figure 12B:
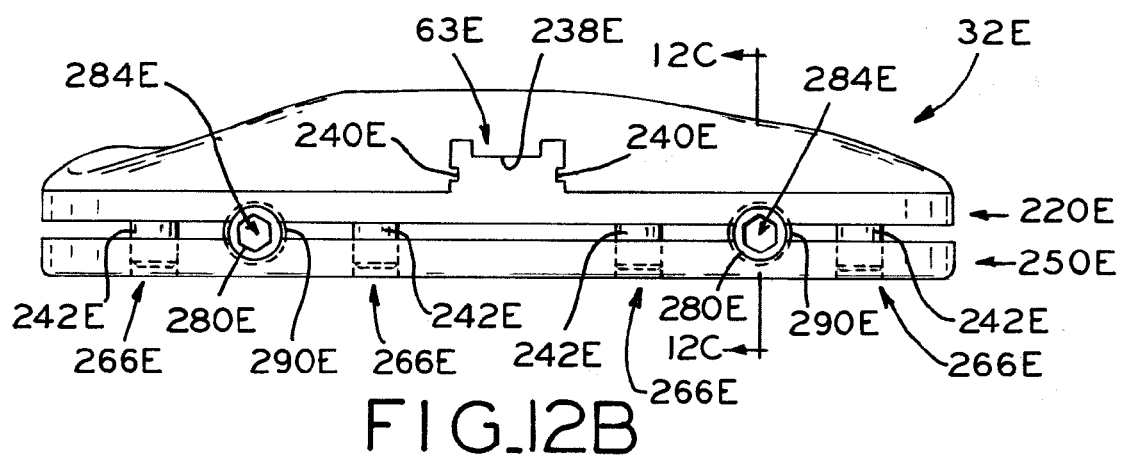
FIG. 12B is a front elevation view of the provisional tibial prosthesis system of FIG. 12A.
Figure 12C:
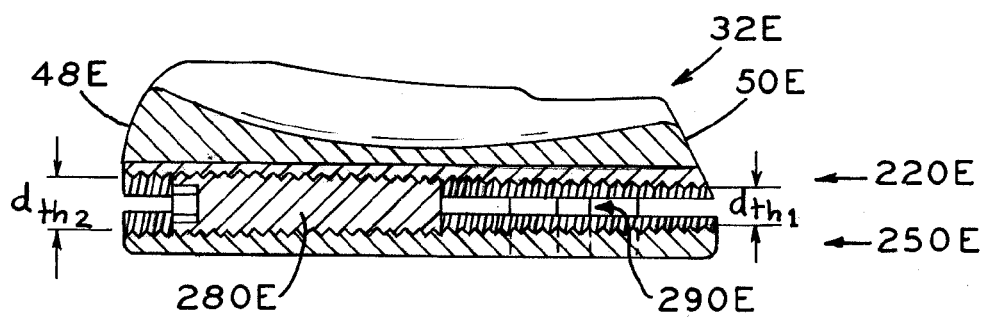
FIG. 12C is a cross-sectional view taken along line 12C-12C of FIG. 12B.

FIGS. 12A-12C illustrate an exemplary fifth embodiment. Exemplary fifth embodiment provisional tibial prosthesis system 30E includes tibial bearing component 32E, upper base component 220E, lower base component 250E, and tapered screws 280E. Upper base component 220E generally includes upper base component inferior surface 222E, opposing upper base component superior surface 224E, upper base component peripheral wall 226E extending from inferior surface 222E to superior surface 224E, anterior side 228E, posterior side 230E, lateral side 232E, and medial side 234E. Tibial bearing component inferior surface 42E includes central notch 61E extending from anterior side 48E towards posterior side 50E and having rail 63E extending distally from inferior surface 42E. In the illustrated embodiment, two protuberances 65E extend from side wall 67E into central notch 61E at a posterior end of central notch 61E.

Upper base component 220E further includes protruding member 236E extending proximally from superior surface 224E. Protruding member 236E including slot 238E spanning a proximal most portion of protruding member 236E from anterior side 228E to posterior side 230E. Further, protruding member 236E includes side grooves 240E. Tibial bearing component 32E is positionable on upper base component 220E by positioning rail 63E of tibial bearing component 32E within slot 238E of upper base component 220E. This arrangement will also cause protuberances 65E to lock into respective side grooves 240E. In such an embodiment, when tibial bearing component 32E is positioned atop upper base component 220E, tibial bearing component 32E is locked to upper base component 220E in medial/lateral direction 22 and proximal/distal direction 24. Upper base component 220E includes posts 242E extending distally from inferior surface 222E.

Referring to FIG. 12A, lower base component 250E generally includes lower base component inferior surface 252E, opposing lower base component superior surface 254E, lower base component peripheral wall 256E extending from inferior surface 252E to superior surface 254E, anterior side 258E, posterior side 260E, lateral side 262E, and medial side 264E. Lower base component 250E includes eight apertures 266E spanning from superior surface 254E to inferior surface 252E. Referring to FIG. 12A, upper base component 220E and lower base component 250E are positioned together by inserting posts 242E of upper base component 220E in respective apertures 266E of lower base component 250E.

Inferior surface 222E of upper base component 220E also includes curved lateral groove 244E and curved medial groove 246E, both grooves 244E and 246E being threaded. Further, superior surface 254E of lower base component 250E includes curved lateral groove 268E and curved medial groove 270E, both grooves 268E and 270E being threaded. When upper base component 220E is positioned atop lower base component 250E, curved lateral groove 244E of upper base component 220E and curved lateral groove 268E of lower base component 250E form a first tapered hole 290E (shown in FIG. 12B), and curved medial groove 246E of upper base component 220E and curved medial groove 270E of lower base component 250E form a second tapered hole 290E (shown in FIG. 12B).

Referring to FIGS. 12A-12C, the use of tapered screws 280E to adjust the thickness of provisional tibial prosthesis system 30E, i.e., the distance between upper base component 220E and lower base component 250E, will now be described. Tapered screws 280E generally include external threaded portions 282E and internal female hexagon socket 284E. Tapered screws 280E are threadably inserted into respective tapered holes 290E at anterior side 48E. Tapered screw 280E includes tapered screw diameter $dts_1$ at posterior end 286E and tapered screw diameter $dts_2$ at anterior end 288E, tapered screw diameter $dts_2$ being greater than tapered screw diameter $dts_1$. Further, referring to FIG. 12C, each tapered hole 290E has tapered hole diameter $dth_1$ at posterior side 50E and tapered hole diameter $dth_2$ at anterior side 48E, tapered hole diameter $dth_2$ being greater than tapered hole diameter $dth_1$. Accordingly, as tapered screws 280E are screwed in an anterior to posterior direction, the distance between upper base component 220E and lower base component 250E is increased.

Figure 13A:
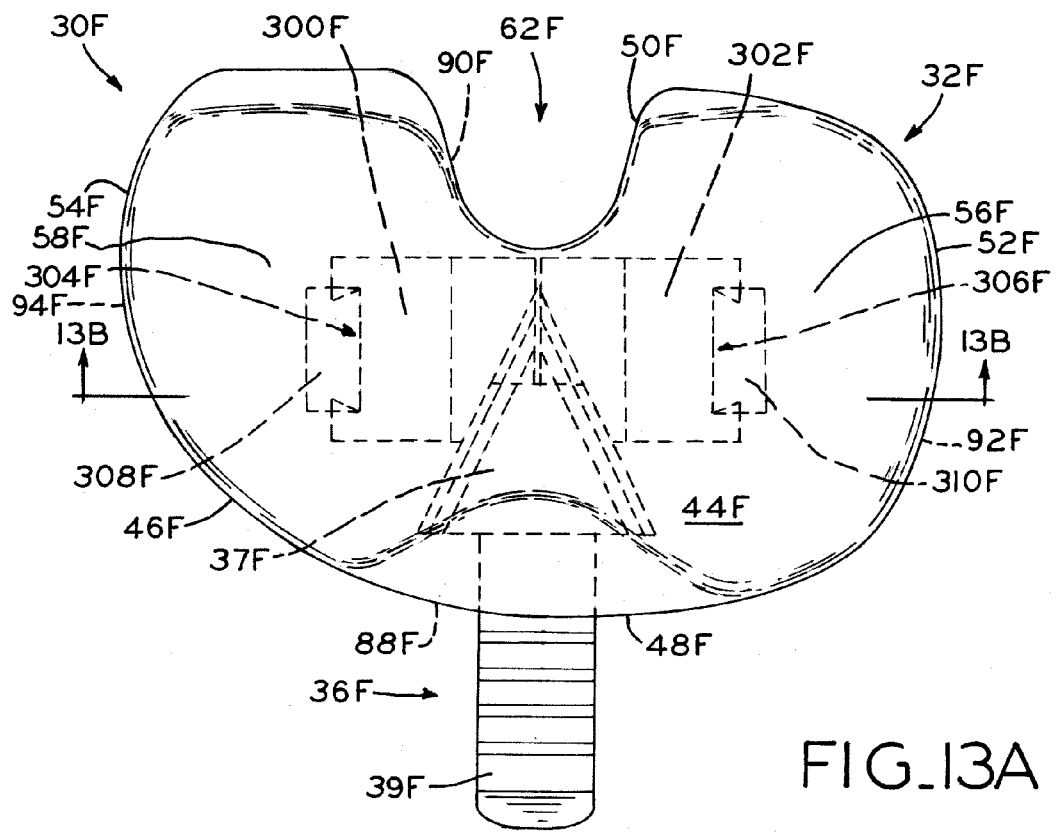
FIG. 13A is a plan view of a provisional tibial prosthesis system in accordance with an exemplary sixth embodiment of the present disclosure.
Figure 13B:
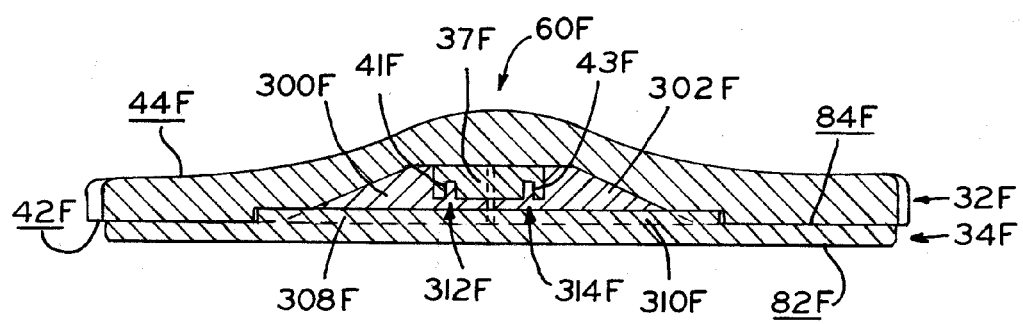
FIG. 13B is a cross-sectional view taken along line 13B-13B of FIG. 13A.

FIGS. 13A and 13B illustrate an exemplary sixth embodiment. Exemplary sixth embodiment provisional tibial prosthesis system 30F includes tibial bearing component 32F, base component 34F, wedge 36F, moving medial member 300F, moving lateral member 302F, medial base rail 308F, and lateral base rail 310F.

Base component superior surface 84F includes medial base rail 308F and lateral base rail 310F. Medial member 300F includes medial member bottom slot 304F and lateral member 302F includes lateral member bottom slot 306F which respectively correspond to medial base rail 308F and lateral base rail 310F. Slots 304F, 306F are respectively positioned atop rails 308F, 310F to secure medial member 300F and lateral member 302F to base component 34F. In an exemplary embodiment, slots 304F, 306F and rails 308F, 310F each have a corresponding dovetail shape and cooperate together to act as a physical barrier to prevent lift-off of medial member 300F and lateral member 302F from base component 34F while allowing medial member 300F and lateral member 302F to move in medial/lateral direction 22 over rails 308F, 310F.

Wedge component 36F generally includes wedge head portion 37F, wedge handle 39F, wedge medial slot 41F, and wedge lateral slot 43F. Wedge component 36F is attachable to medial member 300F and lateral member 302F by aligning wedge medial slot 41F and wedge lateral slot 43F respectively over medial member rail 312F and lateral member rail 314F which allows wedge component 36F to slide in an anterior/posterior direction relative to moving members 300F, 302F. As wedge component 36F is slid in an anterior to posterior direction, wedge head portion 37F pushes medial member 300F and lateral member 302F outward in medial/lateral direction 22 over rails 308F, 310F. In such an embodiment, the inclined surfaces (shown in FIG. 13B) of moving medial member 300F and moving lateral member 302F interface with inferior surface 42F of tibial bearing component 32F causing tibial bearing component 32F to move in a proximal direction away from base component 34F.

FIG. 14 illustrates an exemplary seventh embodiment. Exemplary seventh embodiment provisional tibial prosthesis system 30G includes tibial bearing component 32G, base component 34G, and gear system 36G. Base component superior surface 84G includes anterior post 95G, lateral posterior post 97G, and medial posterior post 99G, posts 95G, 97G, 99G each extending proximally from superior surface 84G.

Gear system 36G generally includes anterior gear 121G, lateral posterior gear 123G, and medial posterior gear 124G. Posterior gears 123G, 124G include annular incline surfaces 125G located on top of gears 123G, 124G. Further, front anterior gear 121G includes front anterior gear teeth 127G, and posterior gears 123G, 124G each include posterior gear teeth 129G. Referring to FIG. 14, front anterior gear 121G is attached to base component 34G by sliding aperture 131G of front anterior gear 121G over anterior post 95G of base component 34G. Similarly, lateral posterior gear 123G is attached to base component 34G by sliding aperture 131G of lateral posterior gear 123G over lateral post 97G of base component 34G and medial posterior gear 124G is attached to base component 34G by sliding aperture 131G of medial posterior gear 124G over medial posterior post 99G of base component 34G.

Referring to FIG. 14, the use of gear system 36G to adjust the distance of tibial bearing component 32G from base component 34G will now be described. The portion of front anterior gear 121G exposed from tibial bearing component 32G and base component 34G at anterior side 88G can be turned by a surgeon's finger or a surgical instrument to turn front anterior gear 121G which causes posterior gears 123G, 124G to rotate. Front anterior gear 121G is mechanically connected to posterior gears 123G, 124G by engagement of front anterior gear teeth 127G with rear posterior gear teeth 129G of lateral posterior gear 123G and medial posterior gear 124G. Rotation of posterior gears 123G, 124G causes annular incline surface 125G of posterior gears 123G, 124G to rotate so the thickest part of annular incline surface 125G starts to contact an inferior surface of tibial bearing component 32G which causes tibial bearing component 32G to move in a proximal direction away from base component 34G.

FIG. 15 illustrates an exemplary eighth embodiment. Exemplary eighth embodiment provisional tibial prosthesis system 30H includes tibial bearing component 32H, base component 34H, pry bar 36H, lateral wing 45H, and medial wing 47H. Base component superior surface 84H includes a plurality of steps 85H that are respectively located a distance closer to an inferior surface of tibial bearing component 32H as steps 85H extend inwardly from medial side 54H and lateral side 52H.

Referring to FIG. 15, the use of exemplary eighth embodiment provisional tibial prosthesis system 30H will now be described. As shown in FIG. 15, pry bar 36H is movably connected to tibial bearing component 32H and base component 34H via support members 41H and pins 43H. In such an embodiment, exerting a force on tab 37H of pry bar 36H pushes up lifting member 39H of pry bar 36H to move tibial bearing component 32H away from base component 34H. As the distance between tibial bearing component 32H and base component 34H increases via pry bar 36H, spring-loaded lateral wing 45H and medial wing 47H rotate inward towards pry bar 36H to the next step 85H. Lateral wing 45H and medial wing 47H maintain the distance between tibial bearing component 32H and base component 34H created by pry bar 36H. If a greater thickness is desired, tab 37H of pry bar 36H can again be depressed causing lifting member 39H of pry bar 36H to further move tibial bearing component 32H away from base component 34H causing lateral wing 45H and medial wing 47H to again rotate inwards to the next level step 85H. In this manner, lateral wing 45H and medial wing 47H again maintain the distance between tibial bearing component 32H and base component 34H created by pry bar 36H.

To reset the distance between tibial bearing component 32H and base component 34H to an initial position, lateral exposed end 49H of lateral wing 45H and medial exposed end 51H of medial wing 47H can be pushed in an outward direction away from pry bar 36H to push lateral wing 45H and medial wing 47H back to the initial position causing tibial bearing component 32H to collapse back to an initial position relative to base component 34H.

Figure 16A:
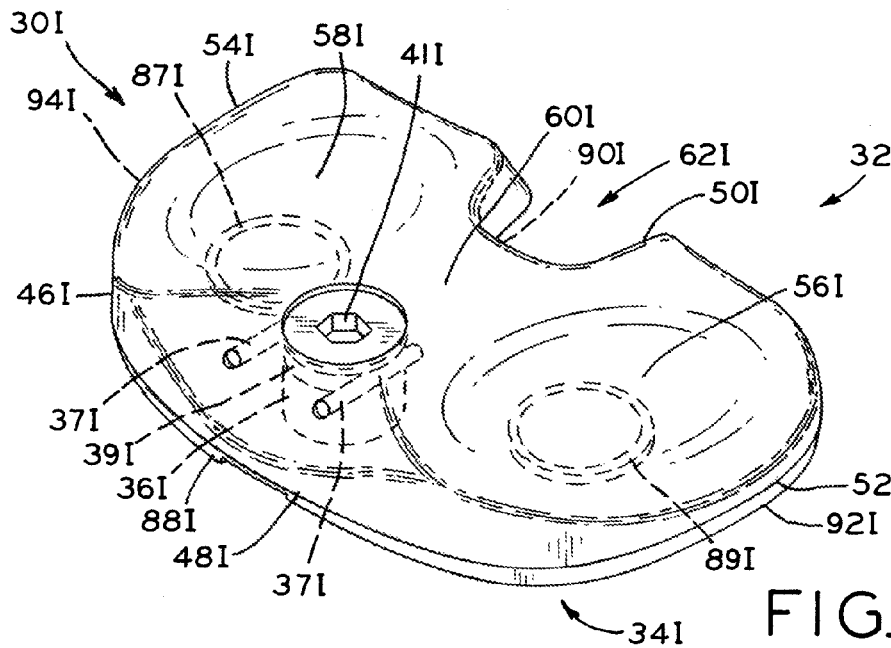
FIG. 16A is a perspective view of a provisional tibial prosthesis system in accordance with an exemplary ninth embodiment of the present disclosure.
Figure 16B:
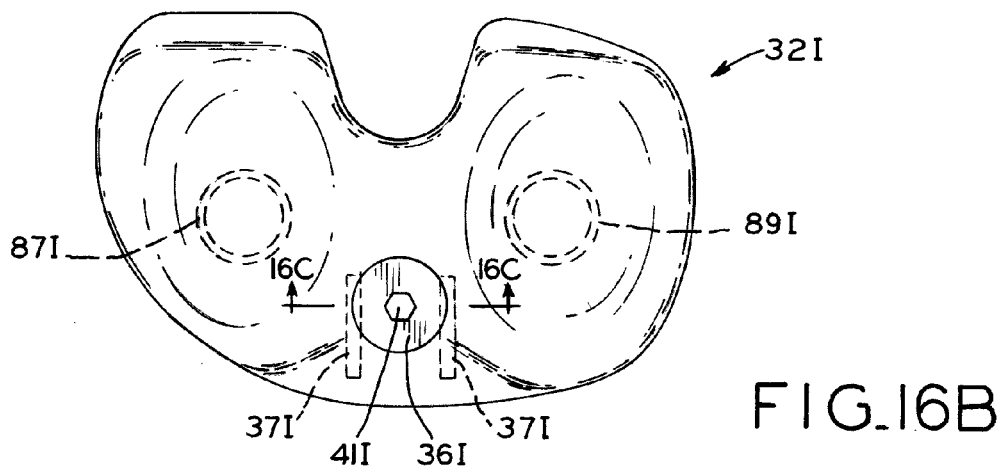
FIG. 16B is a plan view of the provisional tibial prosthesis system of FIG. 16A.
Figure 16C:
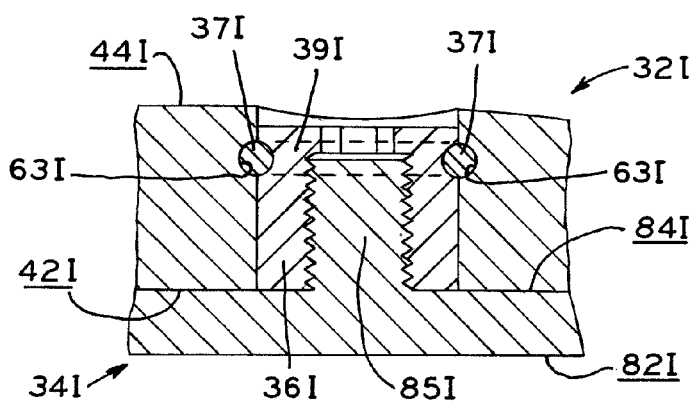
FIG. 16C is a cross-sectional view taken along line 16C-16C of FIG. 16B.

FIGS. 16A-16C illustrate an exemplary ninth embodiment. Exemplary ninth embodiment provisional tibial prosthesis system 30I includes tibial bearing component 32I, base component 34I, threaded cylinder 36I, and locking cylinders 37I. Referring to FIGS. 16A-16C, the use of exemplary ninth embodiment provisional tibial prosthesis system 30I will now be described. Threaded cylinder 36I is positioned between tibial bearing component 32I and base component 34I by threadably attaching threaded cylinder 36I to threaded anterior post 85I extending from base component superior surface 84I. Threaded cylinder 36I is attached to tibial bearing component 32I via locking cylinders 37I. Referring to FIG. 16C, locking cylinders 37I are securely positioned within threaded cylinder annular groove 39I to threaded cylinder 36I, and are also securely positioned within tibial bearing component receiving apertures 63I to tibial bearing component 32I. Locking cylinders 37I prohibit relative axial movement between cylinder 36I and bearing component 32I while allowing relative rotational movement between cylinder 36I and bearing component 32I. Posts 87I, 89I prevent bearing component 32I from rotating relative to base component 34I.

In use, a tool having a hexagonal cross-section can be inserted in internal female hexagon socket 41I of threaded cylinder 36I to rotate threaded cylinder 36I on threaded anterior post 85I of base component 34I. As threaded cylinder 36I rotates and moves away from base component 34I, tibial bearing component 32I which is connected to threaded cylinder 36I via locking cylinders 37I travels with threaded cylinder 36I in a proximal direction away from base component 34I.

Figure 17A:
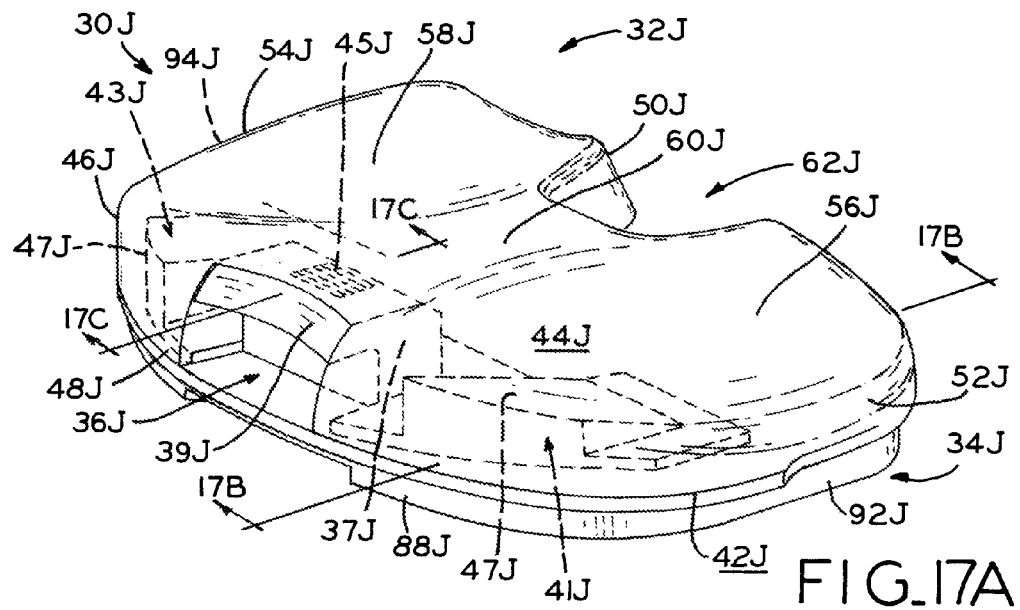
FIG. 17A is a perspective view of a provisional tibial prosthesis system in accordance with an exemplary tenth embodiment of the present disclosure.
Figure 17B:
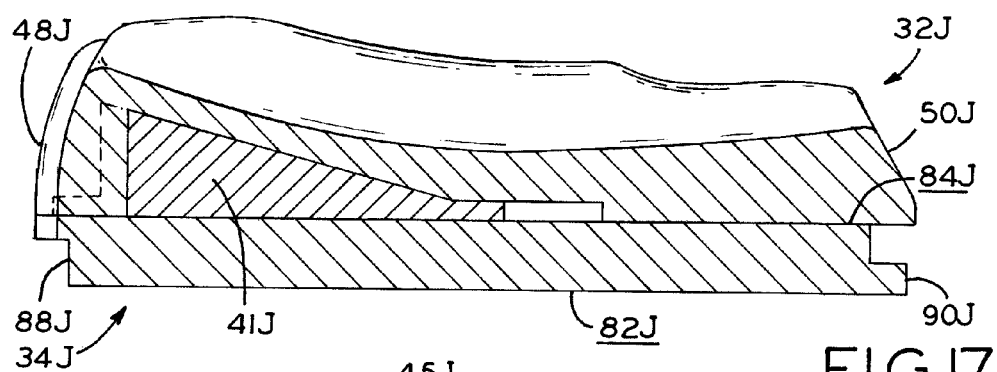
FIG. 17B is a cross-sectional view taken along line 17B-17B of FIG. 17A.
Figure 17C:
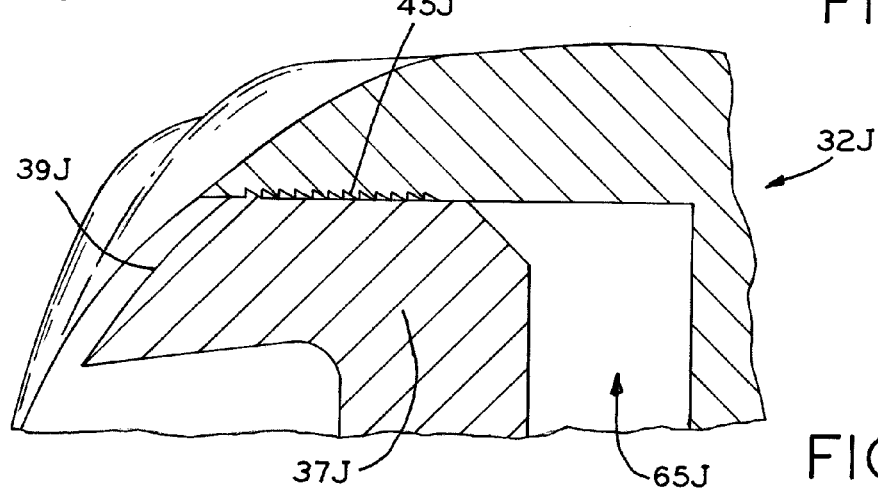
FIG. 17C is a cross-sectional view taken along line 17C-17C of FIG. 17A.

FIGS. 17A-17C illustrate an exemplary tenth embodiment. Exemplary tenth embodiment provisional tibial prosthesis system 30J includes tibial bearing component 32J, base component 34J, and component wedge assembly 36J. Component wedge assembly 36J includes wedge head portion 37J having tab 39J exposed from tibial bearing component 32J, lateral wedge 41J, and medial wedge 43J. Wedge head portion 37J, lateral wedge 41J, and medial wedge 43J form an integral wedge piece that can move in anterior/posterior direction 20 relative to tibial bearing component 32J and base component 34J within tibial bearing component cavity 65J. Referring to FIGS. 17A-17C, the use of exemplary tenth embodiment provisional tibial prosthesis system 30J will now be described. As shown in FIGS. 17A and 17C, as tab 39J is pushed in an anterior to posterior direction, teeth 45J grab a portion of tibial bearing component 32J to prevent wedge assembly 36J from anterior movement when no force is exerted on tab 39J. As tab 39J of wedge head portion 37J is moved in an anterior to posterior direction, attached lateral wedge 41J and medial wedge 43J also move within tibial bearing component cavity 65J in the anterior to posterior direction. As wedge head portion 37J is pushed anterior to posterior, the inclined surfaces 47J of lateral wedge 41J and medial wedge 43J move tibial bearing component 32J away from base component 34J. To reduce the distance between tibial bearing component 32J and base component 34J, a force is exerted on tab 39J to disengage teeth 45J from bearing component 32J and then tab 39J is pulled back toward anterior side 48J to pull component wedge assembly 36J from a posterior to anterior direction, thus decreasing the distance between tibial bearing component 32J and base component 34J.

FIGS. 18A-18B illustrate an exemplary eleventh embodiment. Exemplary eleventh embodiment provisional tibial prosthesis system 30K includes tibial bearing component 32K, base component 34K, rotating knob 36K, medial tapered pin 37K, and lateral tapered pin 39K. Rotating knob 36K is movably connected with medial tapered pin 37K and lateral tapered pin 39K via connecting rod 41K. Further, rotating knob 36K, medial tapered pin 37K, lateral tapered pin 39K, and connecting rod 41K are each positioned between tibial bearing component 32K and base component 34K, and are rotatable relative to tibial bearing component 32K and base component 34K. Inferior surface 42K of tibial bearing component 32K includes curved medial groove 65K and curved lateral groove 67K. Base component superior surface 84K includes corresponding curved medial groove 85K and curved lateral groove 87K which respectively correspond to curved medial groove 65K and curved lateral groove 67K of tibial bearing component 32K to create receiving hole 290K which receives medial tapered pin 37K, lateral tapered pin 39K, and connecting rod 41K.

As shown in FIG. 18A, portion 43K of rotating knob 36K is exposed from tibial bearing component 32K to allow knob 36K to be rotated in a clockwise direction or a counterclockwise direction. Referring to FIGS. 18A and 18B, the use of exemplary eleventh embodiment 30K will now be described. As knob 36K is rotated in a first direction, both medial tapered pin 37K and lateral tapered pin 39K are rotated in receiving hole 290K in a direction towards knob 36K. In such an embodiment, medial tapered pin 37K and lateral tapered pin 39K are tapered such that the end of both medial tapered pin 37K and lateral tapered pin 39K farthest from knob 36K has a diameter greater than the end of medial tapered pin 37K and lateral tapered pin 39K which is closest to knob 36K. For this reason, as knob 36K rotates medial tapered pin 37K and lateral tapered pin 39K toward knob 36K, the end of medial tapered pin 37K and lateral tapered pin 39K which has the greatest diameter is moved inward towards knob 36K to move tibial bearing component 32K away from base component 34K. In the illustrated embodiment, rotation of knob 36K in a second direction, opposite the first direction, will cause medial tapered pin 37K and lateral tapered pin 39K to rotate in a direction away from knob 36K to decrease the distance between tibial bearing component 32K and base component 34K.

While this disclosure has been described as having exemplary designs, the present disclosure can be further modified within the spirit and scope of this disclosure. This application is therefore intended to cover any variations, uses, or adaptations of the disclosure using its general principles. Further, this application is intended to cover such departures from the present disclosure as come within known or customary practice in the art to which this disclosure pertains and which fall within the limits of the appended claims.

What is claimed is:

1. A provisional tibial prosthesis system for a prosthetic knee joint for implantation in a natural knee, the provisional tibial prosthesis system capable of alternatively mimicking the geometry of a first final tibial prosthesis and a second final tibial prosthesis, the natural knee comprising a proximal tibia and a distal femur and having a medial/lateral axis, an anterior/posterior axis, and a proximal/distal axis, the medial/lateral axis corresponding to a medial/lateral direction, the anterior/posterior axis corresponding to an anterior/posterior direction, and the proximal/distal axis corresponding to a proximal/distal direction, the provisional tibial prosthesis system comprising:
   a tibial base plate having a bone contacting surface and an opposing base plate superior surface;
   a tibial bearing component having a tibial bearing component height, said tibial bearing component attachable to said tibial base plate, said tibial bearing component height representing the first final tibial prosthesis;
   a shim having a shim height, said shim slidable relative to both said tibial base plate and said tibial bearing component to be slidably receivable between said tibial base plate and said tibial bearing component in the anterior/posterior direction when said tibial base plate and said tibial bearing component are separated by a distance along the proximal/distal axis equal to said shim height, said shim height cooperating with said tibial bearing component height to represent the second final tibial prosthesis; and
   a base component attachable to said tibial bearing component, said base component positionable between said tibial bearing component and said tibial base plate, said shim slidably receivable between said tibial bearing component and said base component in the anterior/posterior direction when said base component and said tibial bearing component are separated by said distance along the proximal/distal axis equal to said shim height.

2. The provisional tibial prosthesis system of claim 1, further comprising a first lock, wherein when said shim is received between said base component and said tibial bearing component, said first lock locks said tibial bearing component to said base component in the proximal/distal direction, whereby significant relative movement between said tibial bearing component and said base component in the proximal/distal direction is prevented.

3. The provisional tibial prosthesis system of claim 2, further comprising a second lock, wherein when said tibial bearing component is attached to said base component, said second lock locks said tibial bearing component to said base component in the medial/lateral direction and the anterior/posterior direction, whereby significant relative movement between said tibial bearing component and said base component in the medial/lateral direction and the anterior/posterior direction is prevented.

4. The provisional tibial prosthesis system of claim 1, wherein:
   said base component includes a base component inferior surface, an opposing base component superior surface, and a protrusion extending from said base component superior surface, said base component inferior surface positionable on said tibial base plate superior surface; and
   said tibial bearing component includes a tibial bearing component inferior surface and an opposing tibial bearing component superior surface, said tibial bearing component inferior surface having a wall defining a cavity, said cavity sized to accept said protrusion of said base component therein, said cavity sized relative to said protrusion so that said wall cooperates with said protrusion to prevent significant relative movement between said tibial bearing component and said base component in the medial/lateral direction and the anterior/posterior direction.

5. The provisional tibial prosthesis system of claim 1, wherein:
   said tibial bearing component includes a tibial bearing component inferior surface and an opposing tibial bearing component superior surface, said tibial bearing component inferior surface defining a slot; and said shim includes a shim superior surface, an opposing shim inferior surface, and a rail extending from said shim superior surface, said shim removably attachable to said tibial bearing component by sliding said rail of said shim in said slot of said tibial bearing component in the anterior/posterior direction.

6. The provisional tibial prosthesis system of claim 5, wherein said slot of said tibial bearing component and said rail of said shim each have a dovetail cross-sectional shape.

7. The provisional tibial prosthesis system of claim 5, wherein said slot of said tibial bearing component and said rail of said shim each have a T-shaped cross-sectional shape.

8. The provisional tibial prosthesis system of claim 1, wherein:

said base component includes a base component inferior surface, an opposing base component superior surface, and a protrusion extending from said base component superior surface, said protrusion defining an indentation between said protrusion and said base component superior surface, said base component inferior surface positionable on said tibial base plate superior surface; and said shim includes a shim superior surface, an opposing shim inferior surface, a shim anterior side, and a shim posterior side, said shim defining a notch formed in said shim posterior side, said notch spanning said shim superior surface and said shim inferior surface, said shim removably attachable to said base component by sliding said indentation of said base component in said notch of said shim in the anterior/posterior direction.

9. A provisional tibial prosthesis system for a prosthetic knee joint for implantation in a natural knee, the provisional tibial prosthesis system capable of alternatively mimicking the geometry of a first final tibial prosthesis, a second final tibial prosthesis, and a third final tibial prosthesis, the natural knee comprising a proximal tibia and a distal femur and having a medial/lateral axis, an anterior/posterior axis, and a proximal/distal axis, the medial/lateral axis corresponding to a medial/lateral direction, the anterior/posterior axis corresponding to an anterior/posterior direction, and the proximal/distal axis corresponding to a proximal/distal direction, the provisional tibial prosthesis system comprising:

a tibial base plate having a bone contacting surface and an opposing base plate superior surface;

a tibial bearing component having a tibial bearing component height, said tibial bearing component attachable to said tibial base plate, said tibial bearing component height representing the first final tibial prosthesis;

a first shim having a first shim height, said first shim slidable relative to both said tibial base plate and said tibial bearing component to be slidably receivable between said tibial base plate and said tibial bearing component in the anterior/posterior direction when said tibial base plate and said tibial bearing component are separated by a first distance along the proximal/distal axis equal to said first shim height, said first shim height cooperating with said tibial bearing component height to represent the second final tibial prosthesis; and a second shim having a second shim height, said second shim slidable relative to both said tibial base plate and said tibial bearing component to be slidably receivable between said tibial base plate and said tibial bearing component in the anterior/posterior direction when said tibial base plate and said tibial bearing component are separated by a second distance along the proximal/distal axis equal to said first shim height and said second shim height, said first shim height and said second shim height cooperating with said tibial bearing component height to represent the third final tibial prosthesis.

10. The provisional tibial prosthesis system of claim 9, further comprising:

a base component attachable to said tibial bearing component, said base component positionable between said tibial bearing component and said tibial base plate, said first shim slidably receivable between said tibial bearing component and said base component in the anterior/posterior direction when said base component and said tibial bearing component are separated by said first distance along the proximal/distal axis equal to said first shim height, and said second shim slidably receivable between said tibial bearing component and said base component in the anterior/posterior direction when said base component and said tibial bearing component are separated by said second distance along the proximal/distal axis equal to said first shim height and said second shim height.

11. The provisional tibial prosthesis system of claim 10, further comprising a lock, wherein when said tibial bearing component is attached to said base component, said lock locks said tibial bearing component to said base component in the medial/lateral direction and the anterior/posterior direction, whereby significant relative movement between said tibial bearing component and said base component in the medial/lateral direction and the anterior/posterior direction is prevented.

12. The provisional tibial prosthesis system of claim 9, further comprising a lock, wherein when said tibial bearing component is attached to said tibial base plate, said lock locks said tibial bearing component to said tibial base plate in the medial/lateral direction and the anterior/posterior direction, whereby significant relative movement between said tibial bearing component and said tibial base plate in the medial/lateral direction and the anterior/posterior direction is prevented.

13. The provisional tibial prosthesis system of claim 9, further comprising:

a surgical instrument configured to engage with features on at least one of said first shim and said second shim, and configured for use in sliding at least one of said first shim and said second shim between said tibial base plate and said tibial bearing component.

14. A method of determining a size of a final tibial prosthesis for a prosthetic knee joint for implantation in a natural knee, the natural knee comprising a proximal tibia and a distal femur and having a medial/lateral axis, an anterior/posterior axis, and a proximal/distal axis, the medial/lateral axis corresponding to a medial/lateral direction, the anterior/posterior axis corresponding to an anterior/posterior direction, and the proximal/distal axis corresponding to a proximal/distal direction, the method comprising:

selecting a provisional tibial prosthesis system, comprising:

a tibial base plate having a bone contacting surface and an opposing base plate superior surface;

a tibial bearing component having a tibial bearing component height, the tibial bearing component attachable to the tibial base plate; and a first shim having a first shim height, the first shim slidable relative to both the tibial base plate and the tibial bearing component to be slidably receivable between the tibial base plate and the tibial bearing component in the anterior/posterior direction when the tibial base plate and the tibial bearing component are separated by a first distance along the proximal/distal axis equal to the first shim height;

resecting the proximal tibia to form a resected proximal tibia surface;

positioning the bone contacting surface of the tibial base plate on the resected proximal tibia surface;

positioning the tibial bearing component on the tibial base plate;

spacing the tibial bearing component from the tibial base plate by sliding the first shim between the tibial base plate and the tibial bearing component in the anterior/posterior direction, without distracting the femur from the tibia a distance greater than the first shim height;

performing range of motion testing to verify proper sizing of the provisional tibial prosthesis system; and when the testing indicates that the provisional tibial prosthesis system is not properly sized, removing the first shim from between the tibial base plate and the tibial bearing component in the anterior/posterior direction;

selecting a second shim having a second shim height, the second shim slidable relative to both the tibial base plate and the tibial bearing component to be slidably receivable between the tibial base plate and the tibial bearing component in the anterior/posterior direction when the tibial base plate and the tibial bearing component are separated by a second distance along the proximal/distal axis equal to the second shim height, the second shim height different than the first shim height; and spacing the tibial bearing component from the tibial base plate by sliding the second shim between the tibial base plate and the tibial bearing component in the anterior/posterior direction, without distracting the femur from the tibia a distance greater than the second shim height.

15. The method of claim 14, wherein the provisional tibial prosthesis system further comprises a surgical instrument having one or more features configured to engage with corresponding features on at least one of the first shim and the second shim, and the surgical instrument performs at least one of sliding the first shim between the tibial base plate and the tibial bearing component, removing the first shim from between the tibial base plate and the tibial bearing component, and sliding the second shim between the tibial base plate and the tibial bearing component.

16. The method of claim 14, wherein the provisional tibial prosthesis system further comprises a base component attachable to the tibial bearing component, the base component positionable between the tibial bearing component and the tibial base plate, and the first and second shims are slidably receivable between the tibial bearing component and the base component in the anterior/posterior direction when the base component and the tibial bearing component are separated by the first distance along the proximal/distal axis equal to the first shim height.

17. The method of claim 16, wherein the provisional tibial prosthesis system further comprises a first lock, and when the first shim or the second shim is received between the base component and the tibial bearing component, the first lock locks the tibial bearing component to the base component in the proximal/distal direction, whereby significant relative movement between the tibial bearing component and the base component in the proximal/distal direction is prevented.

18. The method of claim 17, wherein the provisional tibial prosthesis system further comprises a second lock, wherein when the tibial bearing component is attached to the base component, the second lock locks the tibial bearing component to the base component in the medial/lateral direction and the anterior/posterior direction, whereby significant relative movement between the tibial bearing component and the base component in the medial/lateral direction and the anterior/posterior direction is prevented.

19. The method of claim 16, wherein the tibial bearing component includes a tibial bearing component inferior surface and an opposing tibial bearing component superior surface, the tibial bearing component inferior surface defining a slot; and the first shim includes a shim superior surface, an opposing shim inferior surface, and a rail extending from the shim superior surface, the first shim removably attachable to the tibial bearing component by sliding the rail of the first shim in the slot of the tibial bearing component in the anterior/posterior direction.

20. A method of determining a size of a final tibial prosthesis for a prosthetic knee joint for implantation in a natural knee, the natural knee comprising a proximal tibia and a distal femur and having a medial/lateral axis, an anterior/posterior axis, and a proximal/distal axis, the medial/lateral axis corresponding to a medial/lateral direction, the anterior/posterior axis corresponding to an anterior/posterior direction, and the proximal/distal axis corresponding to a proximal/distal direction, the method comprising:

selecting a provisional tibial prosthesis system, comprising:

a tibial base plate having a bone contacting surface and an opposing base plate superior surface;

a tibial bearing component having a tibial bearing component height, the tibial bearing component attachable to the tibial base plate; and a first shim having a first shim height, the first shim slidable relative to both the tibial base plate and the tibial bearing component to be slidably receivable between the tibial base plate and the tibial bearing component in the anterior/posterior direction when the tibial base plate and the tibial bearing component are separated by a first distance along the proximal/distal axis equal to the first shim height;

resecting the proximal tibia to form a resected proximal tibia surface;

positioning the bone contacting surface of the tibial base plate on the resected proximal tibia surface;

positioning the tibial bearing component on the tibial base plate;

spacing the tibial bearing component from the tibial base plate by sliding the first shim between the tibial base plate and the tibial bearing component in the anterior/posterior direction, without distracting the femur from the tibia a distance greater than the first shim height; and performing range of motion testing to verify proper sizing of the provisional tibial prosthesis system; and when the testing indicates that the provisional tibial prosthesis system is not properly sized, selecting a second shim having a second shim height, the second shim slidable relative to both the tibial base plate and the tibial bearing component to be slidably receivable between the tibial base plate and the tibial bearing component in the anterior/posterior direction when the tibial base plate and the tibial bearing component are separated by a second distance along the proximal/distal axis equal to the first shim height and the second shim height; and spacing the tibial bearing component from the tibial base plate by sliding the second shim between the tibial base plate and the tibial bearing component in the anterior/ posterior direction, without distracting the femur from the tibia a distance greater than the first shim height and the second shim height.

21. The method of claim 20, wherein the provisional tibial prosthesis system further comprises a surgical instrument having one or more features configured to engage with corresponding features on at least one of the first shim and the second shim, and the surgical instrument performs at least one of sliding the first shim between the tibial base plate and the tibial bearing component, and sliding the second shim between the tibial base plate and the tibial bearing component.

* * * * *